United States Patent [19]
Coassin et al.

[11] Patent Number: 5,462,854
[45] Date of Patent: Oct. 31, 1995

[54] INVERSE LINKAGE OLIGONUCLEOTIDES FOR CHEMICAL AND ENZYMATIC PROCESSES

[75] Inventors: Peter J. Coassin, San Juan Capistrano; Kenneth D. Konrad, Long Beach; Jang B. Rampal, Yorba Linda; Ronald M. Cook, San Rafael, all of Calif.

[73] Assignee: Beckman Instruments, Inc., Fullerton, Calif.

[21] Appl. No.: 50,681

[22] Filed: Apr. 19, 1993

[51] Int. Cl.[6] .................. C12Q 1/68; C12P 19/34; C07H 21/04
[52] U.S. Cl. .................. 435/6; 435/91.2; 536/23.1
[58] Field of Search .................. 435/6, 91.2; 536/23.1; 935/78

[56] References Cited

U.S. PATENT DOCUMENTS

| | | | |
|---|---|---|---|
| 4,683,195 | 7/1987 | Mullis et al. | 435/6 |
| 4,683,202 | 1/1989 | Mullis et al. | 435/91.2 |
| 4,800,159 | 1/1989 | Mullis et al. | 435/172.3 |
| 4,851,331 | 7/1989 | Vary et al. | 435/6 |
| 4,883,750 | 11/1989 | Whiteley et al. | 435/6 |
| 4,988,617 | 6/1991 | Landegren et al. | 435/6 |
| 4,994,370 | 2/1991 | Silver et al. | 435/6 |

FOREIGN PATENT DOCUMENTS

WO91/17239  11/1991  WIPO.
WO91/17270  11/1991  WIPO.

OTHER PUBLICATIONS

Ochman et al., *Genetics* 120, 621–623 (1988).
*The Ligase Chain Reaction in a PCR World*, pp. 5–16; 1991; PCR Methods and Applications, F. Barany.
*Methods & Materials*, pp. 81–86:Feb. 1991; The Journal of NIH Research.
*Formation of Covalent Circles of Lambda DNA by E. Coli Extracts*, pp. 148–155:1967 (vol. 57); M. Gellert.
*Genetic Disease Detection and DNA Amplification Using Cloned Thermostable Ligase*, pp. 189–193:Jan. 1991 (vol. 88); Proc. Natl. Acad. Sci.
*The Enzymatic Repair of DNA, I. Formation of Circular λDNA*, pp. 240–247;Apr. 19, 1967 (vol. 58) Biochemistry: Gefter, Becker, and Hurwitz.
*Specific Enzymatic Amplification of DNA in Vitro: The Polymerase Chain Reaction*; pp. 263–273:1986, Cold Spring Harbor Symposia on Quantitative Biology (vol. L1) K. Mullis, F. Faloona, S. Scharf, R. Saiki, G. Horn, and H. Erlich.
*Specific Synthesis DNA in Vitro via a Polymerase–Catalyzed Chain Reaction*, pp. 335–350; 1987 Methods in Enzymology, (vol. 155) K. Mullis, Fred A. Faloona.
*Hot Prospect for New Gene Amplifier*, pp. 254–257:Nov. 29, 1992, Science (vol. 254) No author stated.
*Triplet Repeat Mutations in Human Disease*, pp. 784–789;May 8, 1992, Science (vol. 256) C. Thomas Caskey.
*DNA Ligase: Structure, Mechanism, and Function*, pp. 790–797:Nov. 29, 1974, Science (vol. 186) I. R. Lehman.
*Human Gene Therapy*, pp. 808–813:May 8, 1992; Science (vol. 256); W. French Anderson.

(List continued on next page.)

*Primary Examiner*—Stephanie W. Zitomer
*Assistant Examiner*—Kenneth R. Horlick
*Attorney, Agent, or Firm*—William H. May; P. R. Harder; Janis C. Henry

[57] ABSTRACT

Inverse Linkage Oligonucleotides ("ILO") useful in enzymatic process are disclosed. Particularly preferred ILOs are amenable to enzymatic elongation from either, or most preferably, both termini. In a particularly preferred embodiment, each terminus of an ILO has an enzymatically functional 3' group. Accordingly, under appropriate conditions and in the presence of, e.g., dNTPs, enzyme, sample DNA, and ILO comprising a first region complementary to a first region of the sample DNA and a second region complementary to a second, different region of the sample DNA, exponential amplification of the sample DNA can be effectuated.

12 Claims, 12 Drawing Sheets

OTHER PUBLICATIONS

*Enzymatic Breakage and Joining of Deoxyribonucleic Acid, I. Repair of Single—Strand Breaks in DNA by an Enzyme System from Escherichia Coli Infected with T4 Bacteriophage*, pp. 1021–1028:Feb. 13, 1967; Biochemistry; Weiss and Richardson

*A Ligase–Medicated Gene Detection Technique*, pp. 1077–1080:Aug. 26, 1988; Science (vol. 241) Landegren, Kaiser, Sanders, Hood.

*Linkage of Polynucleotides Through Prosphodiester Bonds By An Enzyme From Escherichia Coli*, pp. 1426–1433:1967; Biochemistry (vol. 57); Olivera and Lehman.

*Sequence–Selective Recognition of DNA by Strand Displacement with a Thymine–Substituted Polyamide*, pp. 1497–1500; Dec. 6, 1991; Science (vol. 254); P. E. Nielsen.

*Peptide Nucleic Acids (PNA)*. Oligonucleotide Analogues with an Achiral Peptdie Backbone, pp. 1895–1897:1986; J. Am. Chem. Soc., vol. 114, No. 5; M. Egholm.

*Automated DNA Diagnostics Using an ELISA–based Oligonucleotide Ligation Assay*, pp. 8923–8927; Jun. 16, 1990; Proc. Natl. Acad. Sci., vol. 87, D. Nickerson.

*Alzheimer's Disease: A Cell Biological Perspective*, pp. 780–783:May 8, 1992; Science (vol. 256); K. Kosik.

*A Solid–Support Methodology for the Construction of Geometrical Objects from DNA*, 114:2656–2663; J. Am. Chem. Soc., Zhang, Y. & Seeman, N. C.

Immuno–PCR: Very Sensitive Antigen Detection by Means of Specific Antibody–DNA Conjugates, Science 258:120–122 (1992), T. Sano et al.

Antisense Effect of Oligodeoxynucleotides with Inverted Terminal Internucleotide Linkages: A Minimal Modification Protecting against Nucleolytic Degradation, Ortigão, J. F. R. et al., Antisense Research and Developments, 2:129–146 (1992).

*Triple–Helix Formation and Cooperation Binding by Oligodeoxynucleotides with a 3'–3' Internucleotide Junction*, Biochemistry 31:1603–1609 (1992).

*Recognition of Mixed–Sequence Duplex DNA by Alternate–Strand Triple Helix Formation*, Horne, D. A. and Dervan, P. B.; J. Am. Chem. Soc. 112:2435–2437 (1990).

Ono et al., *Biochemistry*, 30, 9914–9921 (1991).

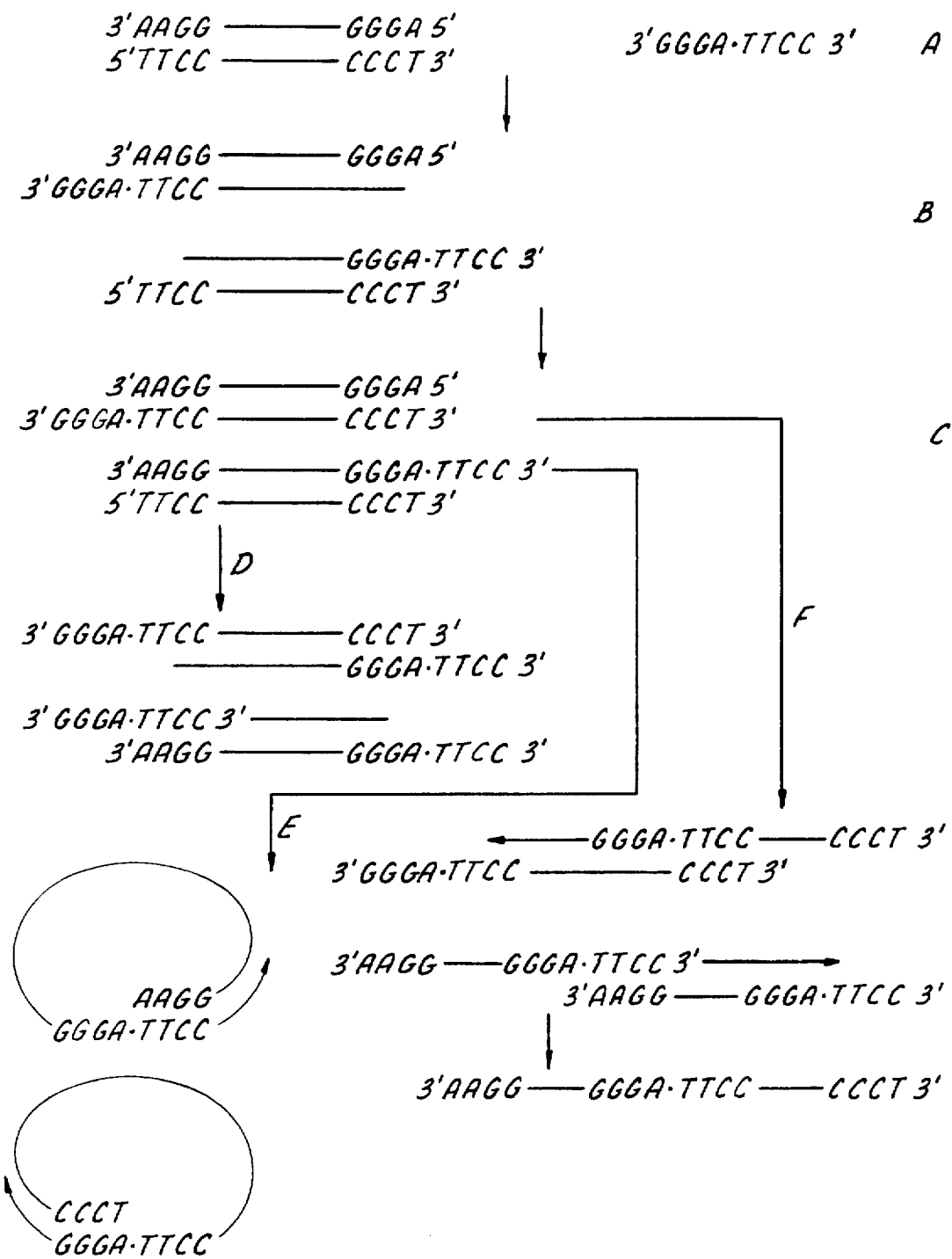

FIG. 2A.

3' GGGT·TTTG 3'

5' CCCA·AAAC 5'

5'———————AAACGGGT———————3'
3'———————TTTGCCCA———————5'

5'———————AAACGGGT———————3'
          GGGT·TTTGCCCA·AAAC

CCCA·AAACGGGT·TTTG
3'———————TTTGCCCA———————5'

3' GGGT·TTTGCCCA·AAAC 5'
5' CCCA·AAACGGGT·TTTG 3'

3' GGGT·TTTGCCCA·AAAC 5'
5' CCCA·AAACGGGT·TTTG 3'

FIG. 2B.

3'- GGGT·GGTTTG - 3'
5'- CCCAGG·AAAC - 5'

5'———————GGAAACGGGTCC———————3'
          GGGT·GGTTTGCCCAGG·AAAC

GGGT·GGAAACGGGT·GGTTTG
3'———————CCTTTGCCCAGG———————5'

Fig. 3.
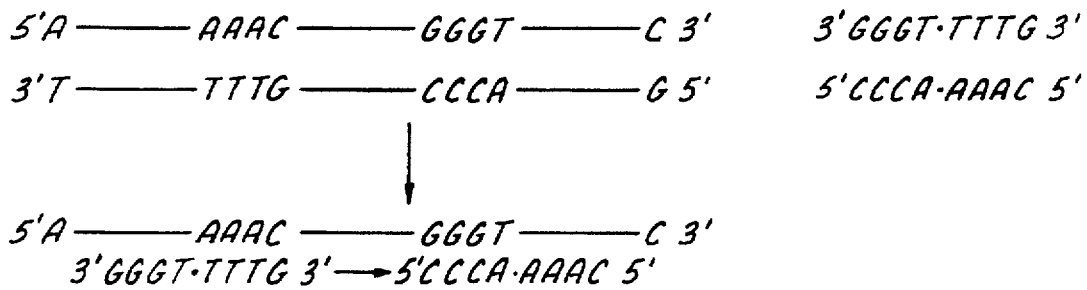
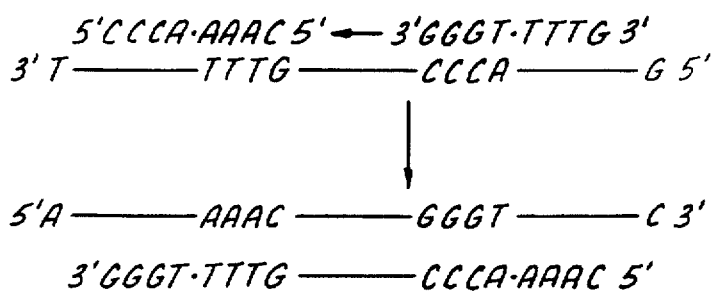
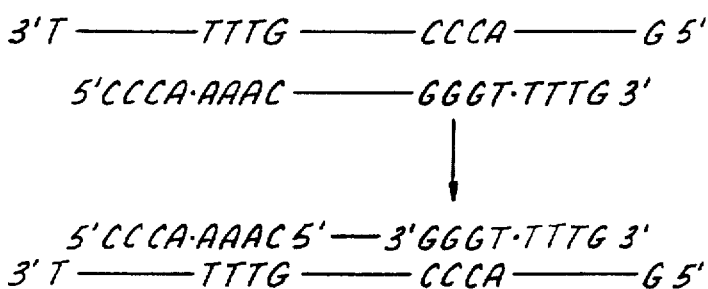
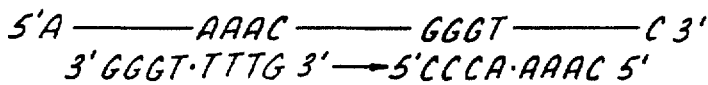
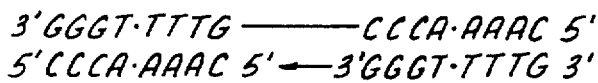
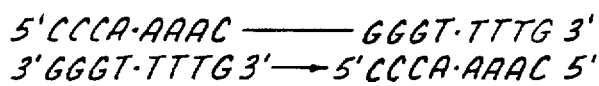

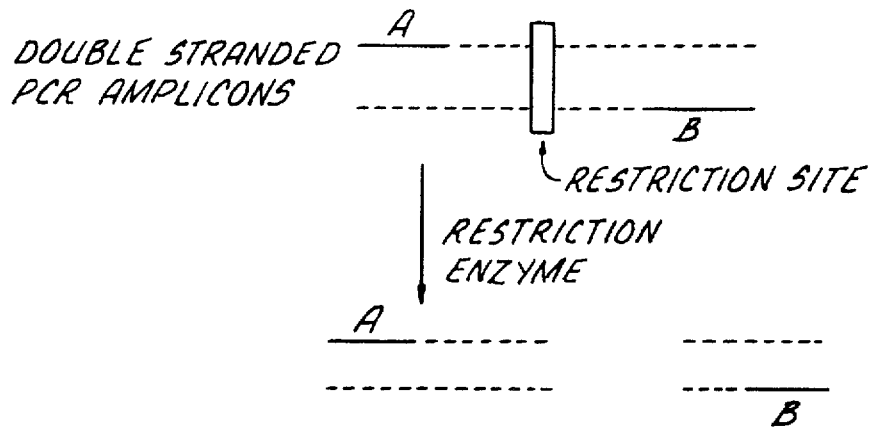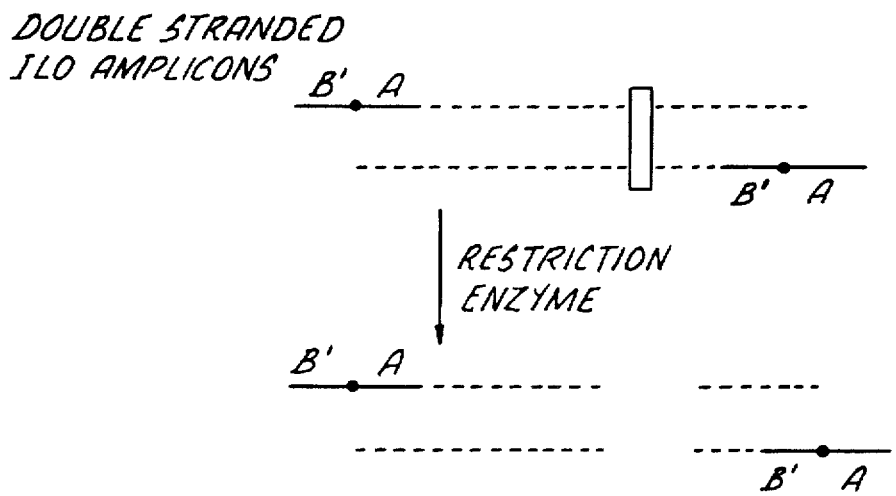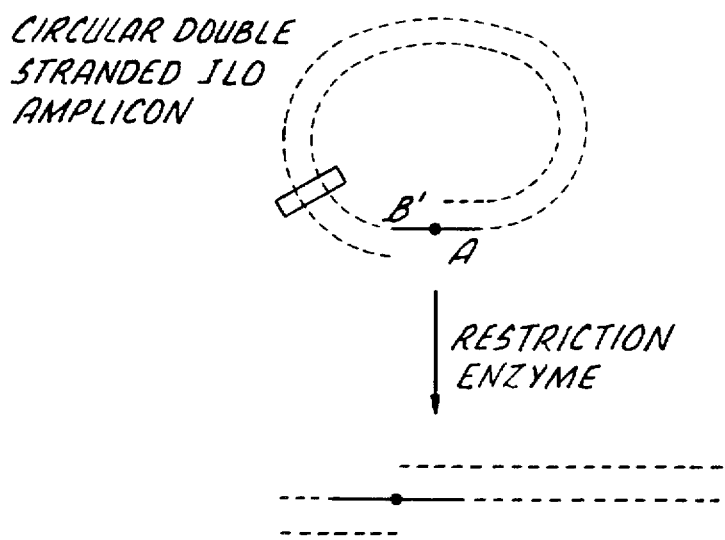
FIG. 11.

FIG. 15.
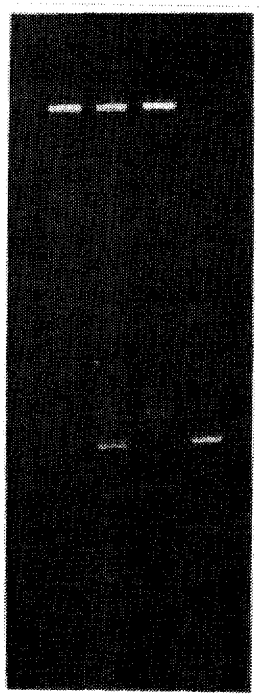 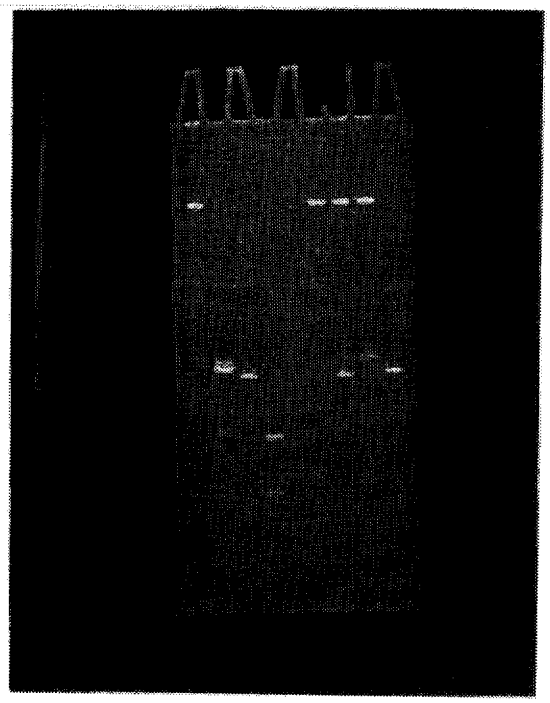
FIG. 16.
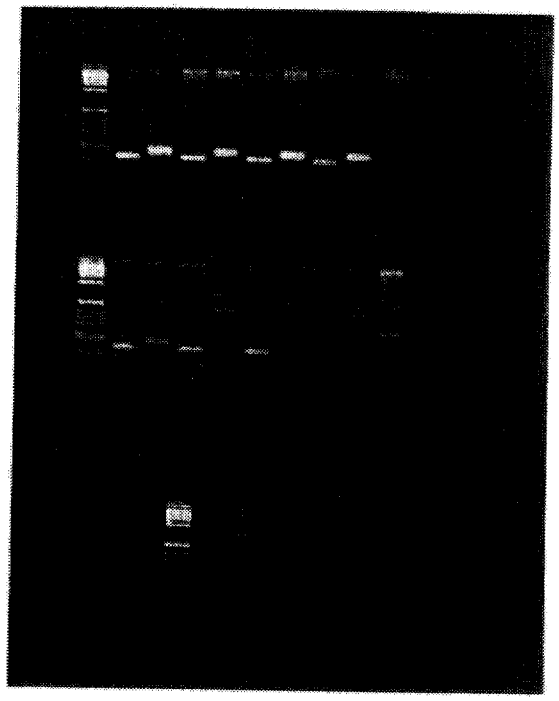

INVERSE LINKAGE OLIGONUCLEOTIDES FOR CHEMICAL AND ENZYMATIC PROCESSES

FIELD OF THE INVENTION

The present invention relates to the synthesis of non-natural oligodeoxyribonucleotides and/or non-natural oligoribonucleotides and their utilization in, e.g., the determination of the presence of specific deoxyribonucleic acid ("DNA") and ribonucleic acid ("RNA") sequences by way of exponential amplification of such non-natural oligodeoxyribonucleotides.

BACKGROUND OF THE INVENTION

The references to be discussed throughout this document are set forth solely for the information described herein prior to the filing date of this document, and nothing herein is to be construed as an admission, either express or implied, that the references are prior or that the inventors are not entitled to antedate such descriptions by virtue of prior inventions or priority based on earlier filed applications.

I. INTRODUCTION

The analysis of deoxyribonucleic acid ("DNA") or ribonucleic acid ("RNA") macromolecules, or regions of interest within DNA or RNA macromolecules, finds utility in a variety of fields. These include, for example, criminal investigations (where DNA from crime scene samples are compared with the DNA from an accused individual); archeology (where the DNA of ancient plants, animals, sub-human species and humans are analyzed); paternity analysis (where the DNA from the offspring and a possible parent are comparatively analyzed); genetic analysis (where the DNA of individuals are analyzed for an indication of the possibility of genetic variation which is indicative of a particular disease state); environmental analysis (where the determination of bacterial contamination of water can be made based upon the presence and quantity of DNA of specified bacterial components); and scientific research. In these exemplary fields, such analysis is nearly impossible without access to sufficient amounts of the DNA and/or RNA; stated again, in order to adequately and efficiently analyze DNA or RNA samples, it is almost an absolute requirement that sufficient amounts of the material must be available to the investigator.

Unfortunately, the amount of DNA and/or RNA available in their native or natural forms is most typically far too minute to allow for efficient analysis thereof. For this reason in particular, it is often essential to sufficiently increase the amount of naturally occurring DNA or RNA obtained from the source thereof in order to conduct such analysis. Generally, sufficiently increasing the amount of such DNA or RNA is referred to as "amplification" or "amplify."

The ability to amplify nucleic acid sequences is relatively recent (1985), but the impact of this ability has been phenomenal. Without the ability to amplify the nucleic acid sequence of interest, most, if not all, of the foregoing non-limiting exemplary fields could not be practiced. Thus, as the areas in which nucleic acid amplification has expanded, the requirements placed upon various amplification techniques have changed.

Accordingly, a very real and ongoing need exists for techniques for the analysis of nucleic acid sequences.

II. NUCLEIC ACID MACROMOLECULES: STRUCTURE, FUNCTION, MUTATION (a) Components Of Nucleic Acid Molecules Deoxyribonucleic acid and ribonucleic acid are long, thread-like macromolecules, DNA comprising a chain of deoxyribonucleotides, and RNA comprising a chain of ribonucleotides. A "nucleotide" consists of a nucleoside and one or more phosphate groups; a "nucleoside" consists of a nitrogenous base linked to a pentose sugar. Typically, the phosphate group is attached to the fifth carbon ("5'") hydroxyl group ("OH") of the penrose sugar; however, it can also be attached to the third-carbon hydroxy group ("3'-OH"). In a molecule of DNA, the pentose sugar is "deoxyribose," while in a molecule of RNA, the penrose sugar is "ribose," The nitrogenous bases in DNA are adenine ("A"), cytosine ("C"), guanine ("G") and thymine ("T"). These bases are the same for RNA, except that uracil ("U") replaces thymine. Accordingly, the major nucleosides of DNA, collectively referred to as "deoxynucleosides," are as follows: deoxyadenosine ("dA"); deoxycytidine ("dC"), deoxyguanosine ("dG"); and thymidine ("T"), The corresponding ribonucleosides are designated as "A"; "C"; "G"; and "U." (By convention, deoxythymidine is typically designated as "T"; for consistency purposes, however, thymidine will be designated as "dT" throughout this disclosure.) The specific sequence of the nitrogenous bases encode genetic information, or, the "blueprint" for life. The primary repeating structures of DNA and RNA molecules can be depicted as the following nucleosides (numbers indicate the positions of the five carbon atoms):

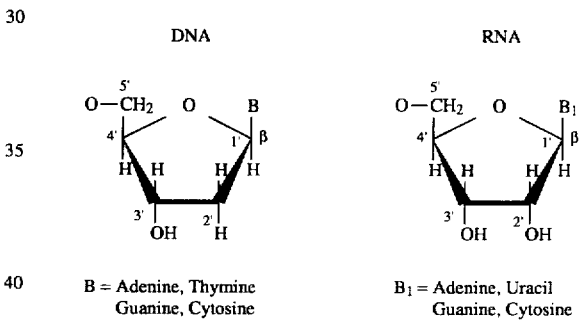

B = Adenine, Thymine Guanine, Cytosine $B_1$ = Adenine, Uracil Guanine, Cytosine (b) Structural Formation While the sequence of the nitrogenous bases of the DNA and RNA macromolecule include genetic information, the sugar and phosphate groups perform a structural role, forming the backbone of the macromolecule. Almost exclusively in nature, biologically-derived DNA is synthesized via linkage of a 5' portion of a first nucleotide to a 3' portion of a second, adjacent nucleotide; the linkage between the two sugars is via a phosphodiester bond. I.e., biological DNA is synthesized in a 5' to 3' direction. For solid-phase, synthetically produced DNA, a starting nucleoside is typically bound by its 3' hydroxy group to a solid support and the 5' hydroxy group is protected, typically with dimethoxytrityl ("DMT"); after the protecting group is removed (typically with mild acid), the next nucleotide is added to the support bound nucleotide via its 3'-OH group.

Double-stranded DNA consists of two "complementary" strands of nucleotide chains which are held together by (relatively) weak hydrogen bonds—these bonds can be broken by, e.g., heating the DNA, changing the salt concentration of a fluid surrounding the DNA, enzymatic manipulation, and chemical manipulation; this process is referred to as "denaturation." By lowering the temperature, readjusting the salt concentration, or removing/neutralizing the enzyme or chemical, the two strands of DNA have a tendency to reform ("anneal") in this approximate/identical original state. The bases of each DNA molecule selectively bind to each other: A always binds with T and C always binds with G. Thus, the sequence 5'-ATCG-3' of a first strand lies immediately opposite a complementary sequence 3'-TAGC-5' (or, by convention, in the 5' to 3' direction, 5'-CGAT-3'). This is referred to as "complementary base pairing" and the process of complementary base pairing is referred to as "hybridization." There are at least three enzymes which can be of importance in the formation of DNA macromolecules: polymerase, which can mediate "elongation" of the macromolecule; and ligase and kinase, which can mediate "repair" of the macromolecule.

The formation of the phosphodiester bond between deoxynucleotides is brought about by the enzyme "DNA-dependent DNA polymerase". In order for DNA polymerase to synthesize a macromolecule of DNA (i.e., "elongation" of the DNA macromolecule), the following components are required: (1) a single stranded DNA molecule, referred to as a "template;" (2) a (typically) short single strand of DNA, having a free 3'-hydroxyl group, which is hybridized to a specific site on the template, this strand being referred to as a "primer;" and (3) free deoxyribonucleotide triphosphates ("dNTP"), i.e. dATP, dCTP, dGTP and dTTP. DNA polymerase can only elongate the primer in a single direction, i.e. from the 3' end of the primer. The primer hybridizes to the template at a region where there can be the requisite complementary base pairing such that the DNA polymerase is capable of bringing about the formation of the phosphodiester bond between the 3'-hydroxyl group of the primer and an "incoming" dNTP which is complementary to the next base on the template. Thus, if the sequence of the template is 5'-ATCG-3' and the primer is 3'-GC-5', the next nucleotide to be added to the 3'-terminus of the primer is the base A (complementary to T on the template) via the formation of a phosphodiester bond, mediated by DNA polymerase, between the dATP and the 3'-hydroxyl group of the G nucleotide on the primer. This process continues (typically) until a complete complement of a region of, or the entire, the template is generated.

While the DNA polymerase enzyme functions principally to elongate a primer strand, the enzymes kinase and ligase function principally to repair single-strand breaks by the formation of the phosphodiester bond between two adjacent nucleotides which are hybridized to a unitary single-strand. Thus, if the sequence of the unitary single-strand is 5'-ATGC-3' and a break has occurred between the A and the C of the complementary strand hybridized thereto, 3'-TAxCG-5' (where "x" indicates the break), the kinase enzyme assists by the addition of a phosphate group at the 5'-end of the A, and ligase enzyme can "repair" the break by the formation of the phosphodiester bond between the A and C. Beneficially, ligase (typically) cannot mediate the formation of such a phosphodiester bond if, inter alia, one of the nucleotides on the strand is not complementary to the nucleotide on the unitary strand, i.e., if the sequence of the unitary strand is 5'-ATCG-3' and the two other strands have the sequences 3'-TA-5' and 3'-TC-5' (the T of the TC strand is not complementary to the C on the ATCG strand), ligase may not mediate the formation of a phosphodiester bond between TA and TC.

(c) Functional Role

DNA, as noted, can be referred to as a "blueprint" for life. The role of DNA is to, inter alia encode amino acids which are the building blocks of proteins, which are necessary to the development, maintenance and existence of living organisms. Three types of RNA (messenger RNA, mRNA; transfer RNA, tRNA; ribosomal RNA, rRNA) are associated with the "translation" of the genetic information encoded in the DNA into designated amino acids. Each of the twenty naturally encoded amino acids is encoded by various groupings of three nucleotides, this grouping being referred to as a "codon." Accordingly, genetic information is generally transferred as follows: DNA→RNA→amino acid/protein.

Not every region of a DNA molecule is translated by RNA into protein; those regions that are translated are referred to as "genes." Expression of genes, therefore, serves to control the translation of hereditary characteristics by specifying the eventual proteins produced from a gene or genes.

(d) Mutations In The Genetic Code

DNA macromolecules are chemically quite similar to each other. A and G are quite similar in chemical composition, and C,T and U are equally similar. Thus, in a specified sequence, substitutions (e.g. transitions) of an A for a G or a C for a T may occur; likewise, transversions of an A or G for a C or T (or vice versa) may occur. When such a substitution occurs within a codon such that the amino acid encoded thereby remains the same, then the substitution can be referred to as a "silent" substitution, i.e., the nucleotides are different but the encoded amino acid is the same. However, other substitutions can alter the amino acid encoded by the codon; when the nucleotide alteration results in a chemically similar amino acid, this is referred to as a "conservative" alteration, while a chemically different amino acid resulting from the alteration is referred to as a "non-conservative" alteration. Non-conservative alterations of amino acids can result in a molecule quite unlike the original protein molecule.

A protein that has had its amino acids altered can be referred to as a "mutant," "mutation" or "variant." Mutations can occur naturally and can have positive, negative or neutral consequences on the organism experiencing such a mutation. Similarly, genes that have had sections altered (e.g., by insertion or deletion of DNA sequence(s)) are mutations; thus, by definition, the protein expressed by such a mutated gene can have positive, negative or neutral consequences on the organism.

III. SYNTHETIC PRODUCTION OF NATURAL OLIGONUCLEOTIDES

Synthetic strands of DNA and RNA are typically referred to as "synthetic oligonucleotides" or "oligonucleotides." While these materials are synthetically produced, unless intentionally altered, they are indistinguishable from DNA and RNA produced by living animals. Thus, a more definitive term is "natural oligonucleotides."

A widely utilized chemical procedure for the synthesis of oligonucleotides is referred to as the "phosphoramidite methodology." See, e.g., U.S. Pat. No. 4,415,732; McBride L. and Caruthers, M. *Tetrahedran Letters* 24:245–248 (1983); and Sinha, N. et al. *Nucleic Acids Res.* 12:4539–4557 (1984), which are all incorporated herein by reference. Commercially available natural oligonucleotide synthesizers based upon the phosphoramidite methodology include, e.g., the Beckman Instruments OLIGO 1000; the Millipore 8750™; and the ABI 380B™, 392™ AND 394™ DNA synthesizers.

The importance of chemically synthesized natural oligonucleotides is principally due to the wide variety of applications to which natural oligonucleotides can be directed. For example, natural oligonucleotides find significant utilization is the use of primers for DNA and RNA amplification techniques such as the polymerase chain reaction, ligase chain reaction, etc., and as probes for detection of the resulting amplification products.

IV AMPLIFICATION TECHNIQUES

There are currently several available techniques for the amplification of nucleic acids. A well known amplification technique is referred to as the "Polymerase Chain Reaction" or "PCR" Mullis, K, et al. "Specific Enzymatic Amplification of DNA In Vitro: The Polymerase Chain Reaction." *Cold Spring Harbor Symposia on Quant. Bio.* 51:263–273 (1986). In the PCR protocol, the template double-stranded DNA is denatured resulting in single strands A and B, "SS-A" and "SS-B". Two primers, one having a sequence complementary to a portion of SS-A, and one having a sequence complementary to SS-B, selectively hybridize to their respective complementary strands. In the presence of DNA polymerase and dNTPs, each primer will be elongated to form complements to the original SS-A and SS-B. Thus, at the end of one such "cycle", the number of "copies" of each strand increases by two—during the next cycle, then, there are two SS-A and two SS-B, each capable of being "copied" as described above. This process is referred to as "exponential" amplification, which means, in essence, that with each cycle, the number of copies double. I.e., theoretically after about 20 cycles, over one million copies are generated ($2^{20}$).

Several practical problems exist with PCR. First, extraneous sequences along the two templates can hybridize with the primers; this results in co-amplification due to such non-specific hybridization. As the level of amplification increases, the severity of such co-amplification also increases. Second, because of the ability of PCR to readily generate millions of copies for each initial template, accidental introduction of the end-product of a previous reaction into other samples easily leads to false-positive results. Third, PCR, does not, in and of itself, allow for detection of single-base changes, i.e. the protocol does not, in and of itself, allow for discrimination between "normal" and "mutational" sequences.

An alternative to PCR is the so-called "Ligase Chain Reaction" or "LCR" Barany, F "Genetic disease detection and DNA amplification using thermostable ligase." *Proc. Natl. Acad. Sci.* 88:189–193 (1991). This technique amplifies a specific target exponentially, based upon utilization of four primers, two for each single strand of the original double-stranded template. Each primer pair hybridizes in an adjacent fashion to each single strand of the template, and ligase covalently joins each primer at the region of adjacent hybridization. As with PCR, the resulting products serve as template (along with the original template) in the next cycle, thus leading to exponential amplification with each cycle. Beneficially, LCR can be utilized to detect mutations, and in particular, single nucleotide mutations—if the primers are designed as complements to the non-mutated version of, e.g., a gene, such that each primer is adjacent to a point where a known mutation can occur, and the template includes such mutation, the ligase cannot covalently couple the two primers that have hybridized thereto.

A problem associated with LCR is that, by definition, the procedure requires four primers which can result in non-specific "blunt-end ligation" of the primers without the need for the presence of target. I.e., there is preferential hybridization of the primers to their respective primer complements rather than the target sequence due to the utilization (most typically) of excess molar concentration of the primers. These double-stranded blunt-end fragments are capable of being ligated even in the absence of target DNA sequences. This can lead to high background signal or false-positive results.

Related to LCR is the so-called "Oligonucleotide Ligation Assay", or "OLA". Landegren, U., et al., *Science* 241:1077–1080 (1988). The OLA protocol relies upon the use of two primers capable of hybridizing to a single strand of a target in an adjacent manner. OLA, like LCR, is particularly suited for the detection of point mutations. Unlike LCR, however, OLA does not result in exponential amplification but rather, "linear" amplification, i.e., at the end of each cycle, only a single end-product (the covalently coupled primers) is produced. A problem associated with OLA, then, is the lack of exponential amplification.

Combining PCR and OLA has been reported as a method of detection. Nickerson, D. A., et al., "Automated DNA diagnostics using an ELISA-based oligonucleotide ligation assay." *Proc. Natl. Acad. Sci. USA* 87:8923–8927 (1990). As reported, the target DNA was exponentially amplified using PCR followed by detection of the amplified target using OLA.

A problem associated with such combinations is that they inherit any problems associated with PCR, plus, by definition, multiple, and separate, processing steps are required.

RNA-based amplification techniques have been described. Guatelli, J. C. et al. "Isothermal, in vitro amplification of nucleic acids by a multi-enzyme reaction modeled after retroviral replication." *PNAS* 87:1874 (1990). This protocol, referred to as "3SR™ amplification," can be utilized to detect gene expressions as the substrate for the reaction is RNA. Beneficially, 3SR, unlike PCR, does not require thermal cycling; as with PCR, the 3SR reaction utilizes two primers which "flank" the region to be amplified. One of these primers must contain a consensus promotor sequence for T7 polymerase. Three different enzymes are required for the 3SR reaction; T7 RNA polymerase; AMV reverse transcriptase; and RNase H. While the benefit of isothermal amplification is possible with 3SR, the requirement for multiple primers and enzymes enhances the potential for problematic application.

The foregoing is to be construed as representative rather than exhaustive. As can be appreciated from the foregoing, however, is that certain of the benefits associated with the amplification protocols also contribute to drawbacks in utilization thereof. One point can be asserted: despite some limitations, particularly in the field of diagnostics, the PCR amplification protocol has enjoyed widespread utilization, principally because of the combination of the power associated with the protocol, as well as the simplicity of the process. Ideally, then, any amplification protocol that is as sensitive as PCR and as specific as, e.g., LCR, but which is easier to perform, would enhance and significantly improve the state of the art.

SUMMARY OF THE INVENTION

The present invention is directed to these needs. In accordance with the invention, disclosed herein are methods for amplifying at least one specific nucleic acid sequence contained in a polynucleotide or a mixture of polynucleotides. The polynucleotide can be a single stranded target as in the case of, e.g., RNA or single strands of DNA, or double-stranded target, as in the case of DNA or DNA-RNA hybrid. Such amplification schemes are based upon utilization of synthetic, non-natural oligonucleotides, referred to herein as Inverse Linkage Oligonucleotides, or "ILO."

ILOs, as disclosed herein for use in target amplification techniques, are nucleic acid molecules having at least two 3' termini, or at least two 5' termini as opposed to a 5' terminus and a 3' terminus. As will be set forth in detail below, ILOs comprising nucleic acid sequences which are complementary to different sections of complementary strands of DNA can be utilized such that ILO extension can proceed from either (or both) termini.

These and other details of the invention will be further elucidated as the disclosure of the invention continues.

BRIEF DESCRIPTION OF THE DRAWINGS

The following drawings are provided for purposes of elucidation and not limitation.

FIG. 1 provides a schematic representation of an enzymatic amplification of a double-stranded target using a 3'-ILO molecule;

FIG. 2A provides a schematic representation of an enzymatic elongation of a 3'-ILO molecule and a 5'-ILO molecule for detection of a mutation along a double-stranded target;

FIG. 2B is an alternative embodiment of the protocol of FIG. 2A where the 3'-ILO and the 5'-ILO each comprises interfering moieties;

FIG. 3 is a schematic representation of an enzymatic elongation and amplification of a double-stranded target sequence, including a gap region, using a 3'-ILO molecule and a 5'-ILO molecule;

FIG. 11 is a schematic representation of cutting of double-stranded PCR amplicon, double-stranded ILO amplicon and Circular Double-Stranded ILO amplicon with restriction enzyme;

FIG. 15 is a photographic reproduction of the results of subjecting PCR amplicons, ILO amplicons and Circular Double-Stranded ILO amplicons to 5' exonuclease; and FIG. 16 is a photographic reproduction of the results of, inter alia, ILO amplification of decreasing concentrations of the same target sequence intermixed with human genomic DNA.

DETAILED DESCRIPTION OF PREFERRED EMBODIMENT

Figure 4:
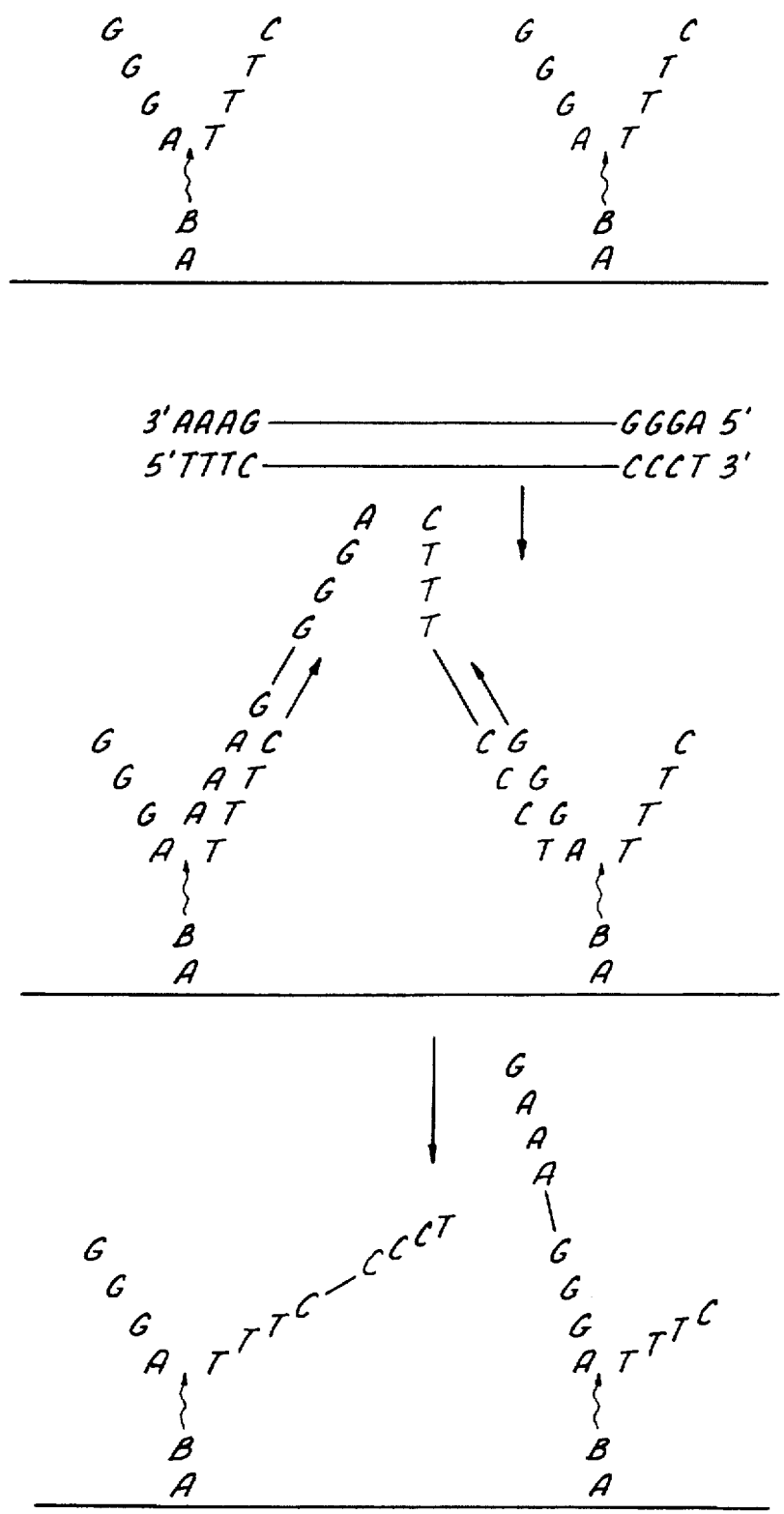
FIG. 4 is a schematic representation of solid phase "elongation" of a double-stranded target sequence using insolubilized 3'-ILO.

The following portion of the disclosure is directed to particularly preferred embodiments of the disclosed invention. Certain terms will be utilized for which definitional elucidation are provided—to the extent that these terms have definitions which may vary from definitions which may be utilized by those in the art, the following definitions apply.

"Chemical Process" when used in conjunction with ILO means a process in which at least one chemical moiety is added to an ILO; typically, the moiety is a nucleotide. The reaction can be covalent or non-covalent.

"Circular Double-Stranded ILO Amplicon" means the product of an Inverse Linkage Oligonucleotide enzymatic amplification process in which an ILO amplicon is of sufficient length and sequence that it is amenable to self-hybridization, or the ILO amplicon self-hybridizes, followed by extension along the extension region of the ILO amplicon from the area of self hybridization to create a complementary sequence of the initial ILO amplicon. The Circular Double-Stranded ILO amplicon is, in actuality, a single-stranded moiety which has certain double-stranded characteristics.

"Elongation" means extension of an Inverse Linkage Oligonucleotide hybridized to a target polynucleotide. Typically, but not always, elongation refers to extension of the ILO via incorporation of deoxynucleotide triphosphates or ribonucleotide triphosphates as mediated by, for example, an Enzymatic Process, or Chemical Process, or by terminal transferase, or by kinase.

"Enzymatic Process" when used in conjunction with ILO means a process in which at least one enzyme catalyzes at least one reaction involving at least one moiety added to an ILO; typically, the moiety is a nucleotide. Enzymatic process includes, but is not limited to, amplification techniques utilizing polymerase enzyme and/or ligase enzyme, reactions such as kinasing reactions, or reactions involving terminal transferase enzyme, or restriction enzymes.

"Fill-in Reaction" refers to the elongation of a first Inverse Linkage Oligonucleotide through the gap region up to another Inverse Linkage Oligonucleotide, where both Inverse Linkage Oligonucleotides are hybridized to the same strand of a target sequence.

"Fully Extended ILO Amplicon" means an ILO amplicon on which all of the termini of the ILO have been extended. A "Fully Extended ILO Amplicon" comprises the same sequence as the original ILO plus at least 50% more nucleotides extending from each termini than the number of nucleotides of the original ILO, e.g., if the original ILO consists of 10 bases on either side of the Inverse Linkage, the Fully Extended ILO Amplicon, owing to the elongation of the original ILO, has at least 15 nucleotides on either side of the Inverse Linkage.

"Gap" means a region between two Inverse Linkage Oligonucleotide moieties which have hybridized to the same strand of a target sequence. A Gap may be from 1 to about 10,000 nucleotides in length.

"Gap Target Sequence" means a target sequence including a region of either partially or fully undefined nucleic acid sequence; preferably, the gap portion of the target is flanked on either side thereof by regions of defined sequence such that Inverse Linkage Oligonucleotide moieties can hybridize thereto, thus providing a gap between the Inverse Linkage Oligonucleotides along the region of the either partially or fully undefined nucleic acid sequence.

"Inverse Linkage" refers to at least one change in the normal orientation of an internucleotidic linkage in a sequence of nucleotides, i.e., 5'A3'-5'G3'-3'T-5'A3' where the underlined region is a 3'-3' Inverse Linkage.

"Inverse Linkage Oligonucleotide" and "ILO" refer to a non-natural oligonucleotide molecule where the orientational 3' to 5' direction of the molecule changes at least once along the length of the molecule. An ILO comprises at least two ends or termini, each terminus having the same primary or secondary hydroxyl group amenable to Enzymatic or Chemical Processes. Thus, a "3'-ILO" is an ILO where each terminus of the molecule is a 3' protected or unprotected hydroxyl group, while a "5'-ILO" is an ILO where each terminus of the molecule is a 5' protected or unprotected hydroxyl group. Most preferably, an ILO is prepared by using both traditional amidites as well as reverse amidites such that at a region within the ILO, at least one 5'-5' and/or 3'-3' Inverse Linkage is created. The number of bases on either side of an Inverse Linkage can be equal or unequal. The Inverse Linkage need not be from one nucleotide directly to another, but can comprise a chemical moiety that links one nucleotide to another nucleotide. An ILO can comprise a Label.

"Inverse Linkage Oligonucleotide Amplicon" and "ILO-amplicon" refer to the extension product of an ILO from at least one terminus of the ILO.

"Inverse Linkage Oligonucleotide Product" and "ILO Product" refer to the end results of a nucleic acid amplification reaction involving ILO.

"Label" means a moiety which is conjugated to an Inverse Linkage Oligonucleotide moiety such that the ILO moiety can be detected or captured. Most preferably, the label is located at the internal 5'-5' or 3'-3' linkage of the ILO. A "directly detectable" label is a signal-producing label which is capable of detection either directly or through its interaction with a substance such as a substrate (in the case of an enzyme), a light source and detector (in the case of a fluorescent compound) or a photomultiplier tube (in the case of a radioactive or chemiluminescent compound). A "proximity label" is one of at least two labels which interact with each other to produce a detectable signal when the proximity labels are brought together. Typically, a first proximity label is used in combination with a corresponding second proximity label. An "indirectly detectable" label is a substance which in and of itself does not provide a signal but which can be utilized to identify an ILO to which the indirectly detectable label is attached. E.g., biotin can be an indirectly detectable label, whereby labelled or insolubilized avidin is used in conjunction therewith—in the first instance, labelled avidin will bind to moieties comprising biotin such that the complex can be directly detected; in the second instance, the biotinylated moiety is insolubilized via the insolubilized avidin, thus allowing for separation, and hence, detection, thereof. Most preferably, the label is directly or indirectly conjugated to the linkage region of the ILO.

"Ligation" means the covalent attachment of one Inverse Linkage Oligonucleotide moiety to at least one other ILO moiety or oligonucleotide moiety. Ligation includes enzymatic processes such as those utilizing a ligase, as well as chemical processes including, but not limited to, chemical reactions, photochemical reactions (e.g. photocoupling; see, e.g. WIPO Publication No. WO 90/01069, publication date of Feb. 8, 1990 incorporated herein by reference), thermochemical and redox reactions.

"Multimeric ILO Amplicon" and "MIA" refer to concatamers between complementary regions of constituent species comprising ILO, and/or Partially Extended ILO Amplicon, and/or Fully-Extended ILO Amplicon, and/or Circular Double Stranded ILO Amplicon. The resulting concatamers can be denatured into their constituent species.

"Partially Extended ILO Amplicon" means an ILO Amplicon in which at least one, but not all, of the termini of the ILO has been extended. A "Partially Extended ILO Amplicon" comprises the same sequence as the original ILO plus at least 50% more nucleotides extending from each of at least one, but not all, termini than the number of nucleotides of the original ILO, e.g., if the original ILO consists of 10 bases on either side of the Inverse Linkage, the Partially Extended ILO Amplicon, owing to the elongation of the original ILO from one termini thereof, has at least 15 nucleotides on one side of the Inverse Linkage, and 10 bases on the other side of the Inverse Linkage.

"Reverse amidite" and "reverse phosphoramidite" mean a nucleotide which can be utilized in the formation and an Inverse Linkage Oligonucleotide. Most preferably, a reverse amidite comprises a dimethyoxytrityl ("DMT") or similar protecting group at the 3'-hydroxyl of a deoxynucleoside and a phosphate group at the 5'-hydroxyl of the deoxynucleotide such that the 5' region of the reverse amidite is amenable for linkage to a 5'-OH or 3'-OH of another nucleoside, nucleotide, oligonucleotide, amidite or reverse amidite.

"Substantially" when used in conjunction with ILO Amplicon and Circular Double-Stranded ILO Amplicon means that at least 51% of the ILO product resulting from an exponential amplification of a target sequence using ILOs are Circular Double-Stranded ILO amplicons; more preferably, at least about 60%; and most preferably, at least about 75%.

"Target Sequence" means a defined nucleic acid sequence, the presence or absence of which is desired to be detected. The target sequence can be from any source which comprises DNA and/or RNA, i.e. the source of the target sequence is not limited to mammals. Preferably, the target sequence forms part of a coding region in a gene associated with a genetic disease. For many genetic diseases, such as sickle cell anemia, the presence of a genetic mutation is characterized by small changes in the coding sequence of a gene; typically, individuals who have the genetic disease in question have genes whose sequences differ by as few one nucleotide from the corresponding sequences of these who do not have the disease. The "normal" or the "mutant" gene region can serve as the target sequence. Target sequence can include a "Gap Target Sequence".

"Traditional amidite" and "traditional phosphoramidite" and "amidite" all mean a nucleotide which can be utilized in the formation of an Inverse Linkage Oligonucleotide. Most preferably, a traditional amidite comprises a dimethoxytrityl ("DMT") or similar protecting group at the 5'-hydroxyl of a deoxynucleotide and a phosphate, phosphite or phosphonate group at the 3'-hydroxyl of the deoxynucleotide such that the 3'-region of the amidite is amenable for linkage to a 5'-OH or 3'-OH of another nucleoside, nucleotide, oligonucleotide, amidite or reverse amidite.

Disclosed herein are 3' and 5' Inverse Linkage Oligonucleotides ("ILO") useful for chemical and enzymatic processes, such as, most preferably, nucleic acid amplification techniques involving polymerase and/or ligase enzymes. Because of the unique characteristics of ILOs vis-a-vis such enzymatic processes, efficiency of the processes are beneficially enhanced. In our most preferred ILO-based enzymatic process, we are able to achieve exponential amplification of a nucleic acid macromolecule using a single set of ILO molecules with each ILO in the set having the identical sequence. We have discovered that because of the characteristics of the ILO, the resulting amplification products ("ILO products") have unique features, i.e. self-priming capabilities which lead to products referred to as Circular Double-Stranded ILO amplicons; MIA formation; and solid-phase extension along a target sequence. These features will be highlighted in detail below.

Although not wishing to be bound by any particular theory, our amplification process appears to generate more end-product compared to a PCR reaction, all other conditions being equal; stated again, we appear to be able to achieve substantially equivalent amplification of the same target sequence using less ILO (compared to PCR primers) or less available target sequence. We believe that this is due to the postulated theory that while both ILO and PCR primers "walk" along the target sequence until a complementary section of the target is located, an ILO, because it is a single molecule which comprises at least two regions which are complementary to two different regions of the target sequence, has a statistically greater chance of hybridizing to the target than each of the two PCR primers. Therefore, the ILO process is more robust and more efficient than the PCR process. Given that a significant benefit of the PCR process lies in the inherent ease of use, any other process which is inherently more robust/efficient and as easy to use is, by definition, significantly advantageous vis-a-vis other amplification techniques.

While the following portion of the disclosure provides information regarding preferred embodiments of ILOs utilized in conjunction with enzymatic-amplification of nucleic acid macromolecules, it is to be understood that the utilization of ILO as disclosed herein is not limited to enzymatic-amplification techniques; rather, those skilled in the art will readily appreciate chemical and other enzymatic techniques to which ILOs are applicable.

The arena of so-called anti-sense oligonucleotides has recently generated excitement in, principally, the pharmaceutical-based industry because these molecules have the potential for regulation of gene expression. Antisense oligonucleotide compounds with 3'-3' and 5'-5' inversions have been described as being capable of inhibiting and modulating gene expression. Ramalhu-Ortigão, J. F. L. et al "Antisense Effect of Oligodeoxynucleotides with Inverted Internucleotide Linkages" *Antisense Res. & Dev.* 2:219–146 (1992); see also Froehler, B. C. "Triple-Helix Formation and Cooperative Binding by Oligodeoxynucleotides with a 3'-3' Internucleotide Junction" *Biochem.* 31:1603–1609 (1992) and Horne, P. D. & Dervon, P. B. "Recognition of Mixed-Sequence Duplex DNA by Alternate-Strand Triple-Helix Formation." *J. Am. Chem. Soc.* 112:2435–2437 (1990) (hereinafter collectively referred to as "antisense references"). Exploitation of such molecules has heretofore been directed, as noted, to the arena of pharmaceutical-based antisense manipulation; this is apparently based upon the increased resistance against nucleotylic degradation occasioned by these molecules. See Ramalho-Ortigão, supra.

Traditional phosphoramidites utilized in the synthesis of natural oligonucleotides comprise (most typically) a DMT protecting group at the 5' hydroxyl such that the 3' hydroxyl group of an incoming nucleotide can be conjugated to the 5'-hydroxyl group (once, of course, the DMT group is removed). This allows for conventional 5' to 3' synthesis of natural oligonucleotides.

Polymerase enzyme extends a nucleic acid primer which has hybridized to a target sequence along the primer from the 3' terminus of the primer; thus, with a conventional natural oligonucleotide primer, elongation of the primer occurs in only one direction, i.e. from the 3' terminus. In considering this fact, we approached the desire to define nucleic acid enzymatic-based amplification techniques from an unconventional starting point, i.e., utilization of non-natural oligonucleotides comprising 3'-termini and/or 5'-termini; we refer to these molecules as Inverse Linkage Oligonucleotides, or, conveniently, ILO. Because ILO comprise at least two 3', or at least two 5' termini, they are quite unlike natural oligonucleotides which comprise a single 3' terminus and a single 5' terminus. As such, ILOs are amenable to manipulation in processes quite unlike those in which conventional natural oligonucleotides are utilized.

For example, ILO molecules, each having the same sequence, can be utilized in the exponential amplification of a nucleic acid sequence of interest. If the following non-limiting, schematic representation of a double-stranded target sequence is presented:

| | |
|---|---|
| 5'  ATCG ATTT ACCC AGGG  3' | STRAND A |
| 3'  TAGC TAAA TGGG TCCC  5' | STRAND B | an ILO molecule having the sequence

| | |
|---|---|
| 3'  GCTA·CCCT  3' | 3'-ILO | can be utilized in conjunction with polymerase enzyme and sufficient dNTPs to achieve exponential amplification of the target sequence. (Throughout the remainder of this disclosure the symbol "•", when appearing within an ILO, will symbolize an Inverse Linkage). It is the double 3' termini of the ILO that allows this process to be realized.

Focusing on STRAND A and the above 3'-ILO, the following hybridized moiety is generated:

| | |
|---|---|
| 5'  ATCGATTTACCCAGGG  3' | STRAND A |
| 3'     TCCC·ATCG  3'ILO | | such that under the appropriate conditions, enzymatic elongation of the ILO along STRAND A can be effectuated, resulting in the following Partially Extended ILO Amplicon (STRAND A'):

| | |
|---|---|
| 3'  TCGCTAAATGGGTCCC·ATCG  3' | STRAND A' |

Similarly, the following Partially Extended ILO Amplicon (STRAND B') is derived from STRAND B:

| | |
|---|---|
| 3'  TAGCTAAATGGGTCCC  5' | STRAND B |
| 3'  TCCC·ATCG  3' | ILO |

| | |
|---|---|
| 3'  TCCC·ATCGATTTACCCAGGG  3 | STRAND B' |

As will be appreciated, the reaction products (STRANDS A' and B'), along with STRANDS A and B, can serve as target templates during subsequent rounds in the process:

```
3'  TAGCTAAATGGGTCCC-ATCG  3'              STRAND A'

3'  TCCC-ATCG  3'                           ILO
                    ↓
3'  TCCC-ATCGATTTACCCAGGGTAGCTAGC  3'      STRAND A"

3'  TCCC-ATCGATTTACCAGGG  3'                STRAND B'

3'  TCCC-ATCG  3'             ILO
                    ↓
3'  TAGCTAAATGGTCCC-ATCG  3'                STRAND B"
```

Because STRANDS A and B are also available during this round, exponential amplification of the target sequence is viable.

The ILO amplicons can also take part in the formation of concatamer species, referred to as "Multimeric ILO Amplicons." These species are held together by the relatively weak hydrogen (chemical) bonds associated with base pairing such that under denaturing conditions, MIA can be separated into their constituent parts:

```
TCCC-ATCGATTTACCAGGG   TAGCTAAATGGGTCC-ATCG

TCCC-ATCG
```

The ILO amplicons which result from enzymatic elongation of ILO along target sequences possess a unique feature that is directly attributed to the utilization of ILO molecules—under appropriate conditions which allow for extension of the ILO along the target sequence, one terminus of the extended ILO amplicon is complementary to the non-extended terminus of the ILO amplicon. Accordingly, ILO amplicons are capable of self-priming, i.e. when the termini of an ILO amplicon hybridize, "internal" extension along the ILO amplicon can be effectuated.

This feature allows for the formation of a sub-population of ILO products during target sequence amplification, which we refer to as "Circular Double-Stranded ILO amplicons." We have determined that this product is formed depending upon, e.g., the length of the target sequence.

For example, focusing on STRAND A', it is noted that the termini thereof are complementary to each other such that, with appropriate distance between the termini, self-hybridization can result (for presentational convenience, only the complementary portions are presented):

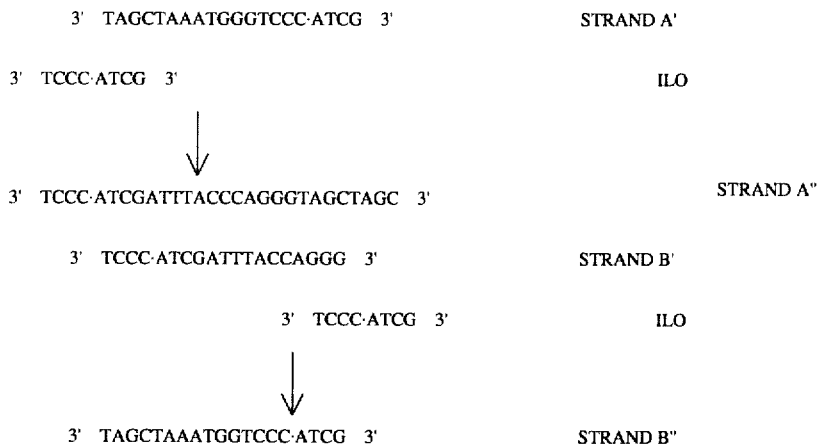

As will be appreciated, this product is amenable to self-priming at the 3' terminus of the ATCG portion of the extension product in the indicated direction (as will also be appreciated, because of the 5'-5' Inverse Linkage, elongation of TAGC from the 3'-termini may not be possible). Thus, a "Circular Double-Stranded ILO amplicon" can be generated.

The ILO amplicons can serve as templates such that both 3' termini of the same ILO amplicon can participate in an elongation reaction. For example, and again focusing on STRAND A', it will be appreciated that STRAND B can hybridize thereto:

```
3'  TAGCTAAATGGGTCCC·ATCG  3'                    STRAND A'

3'  TAGCTAAATGGGTCCC  5'           STRAND B
``` such that STRAND A' can then be elongated towards the 5' termini of STRAND B to generate a Fully Extended ILO amplicon (STRAND A'''):

```
3'  TAGCTAAATGGGTCCC·ATCGATTTACCCAGGG  3'        STRAND A'''
```

We have experimentally determined that the formations of ILO amplicons, Circular Double-Stranded ILO amplicons, or both, can be related to the length of the target sequence. We have found that, as a general proposition (and not a limitation), the "shorter" the length of the target, the "greater" the tendency that the majority of resulting products will be Circular Double-Stranded ILO amplicons, and as the target sequence increases, formation of approximately equivalent amounts of both Circular Double-Stranded ILO amplicons and ILO amplicons can occur.

The length of the ILO utilized in an enzymatic process is dependent principally upon the target sequence and the needs of the investigator. For example, if a specific gene or gene segment is being targeted, knowledge of the sequence thereof allows for the creation of an ILO Which can selectively hybridize in a complementary or substantially complementary fashion, or, if necessary, with absolute complementarity. Such hybridization impacts the melting temperature of the resulting target strand:ILO hybridization product, as well as the sequence of the ILO. The skilled artisan is readily credited with the ability to discern these factors which affect the degree of hybridization and melting temperature.

Because the ILO comprises regions which hybridize to different target sequences, the length of the ILO is amenable to a large degree of flexibility. For example, it is acceptable to utilize ILO which do not have the same number of bases on either side of the Inverse LInkage; however, we prefer that the length of bases on either side of the linkage be substantially identical (i.e. ±10%). This preference is predicated upon the recognition that when all conditions are "equal," a "longer" oligonucleotide will hybridize to a target sequence "faster" then a "shorter" oligonucleotide; thus, by utilizing an ILO where the length of the bases on either side of the linkage are substantially identical, reaction kinetics can be substantially controlled. Accordingly, we prefer a ratio of the length of the regions of the ILO on either side of the linkage to be between about 1:1 and about 1:3, more preferably between about 1:1 and about 1:2, and most preferably 1:1.

The length of the ILO can be between about 8 and about 100 bases in length, preferably between about 15 and about 80 bases in length, and most preferably between about 20 and about 70 bases in length; again, it is our preference that one-half of the length of the ILO hybridize to one region of a target sequence and the other-half of the ILO hybridize to a different region of a target sequence. It is to be understood, however, that the choice of ILO length, and the internal hybridization regions of each ILO are matters of design choice amenable to optimization by those in the art based upon, inter alia, the stringency conditions of the reaction. For convenience, in certain of our Examples we have utilized ILOs having a length of 50 bases, with a 1:1 length ratio of the regions on either side of the inverse internucleotide linkage.

When the target sequence is unknown or only partially known, sufficient information regarding a portion of the sequence "flanking" the target region or of the target region itself is necessary to create an ILO having regions which are complementary to these portions flanking the target, or of the target itself. When the target sequence is unknown or only partially known, the length of the ILO can be beneficially increased to maximize hybridization thereof to the known regions of sequence on the target; this helps to insure correct target sequence hybridization. Again, those skilled in the art are readily credited with optimizing suitable ILO in such situations.

The ILO can be generated using standard techniques and instruments, with the exception that reverse amidites are necessary for a portion of the ILO. For example, using phosphoramidite chemistry in conjunction with commercially available DNA synthesizers, a first portion of the ILO can be generated. This portion comprises the conventional S-3'-5' oligonucleotide, where "S" is a solid support. Thereafter, the reaction column can be removed and placed onto a different instrument which includes reverse phosphoramidites; using this instrument, the complete ILO can be generated as the first reverse amidite added to the reaction chamber will create the inverse internucleotide linkage, followed by addition of the remaining reverse amidites. As will be appreciated, the first portion of the ILO can utilize the reverse phosphoramidites such that the portion attached to the solid support will be as follows: S-5'-3', followed by traditional phosphoramidites. Thus, 3' ILO and 5' ILO molecules can be generated. It is to be understood that a single instrument can be utilized to generate the ILO; preferably, such an instrument has the capability of adding both traditional and reverse phosphoramidites to the reaction chamber.

Chemical linkers can also be utilized for the Inverse Linkage. For example, TOPS™ reagents (Cambridge Research Biochemicals) can be utilized for the linkage of a reverse amidite to a an amidite.

The preferred synthesis protocol utilized to generate reverse phosphoramidites necessitates utilization of a "temporary" protecting group at the 3' hydroxyl group of the deoxynucleotide or deoxynucleoside, such that a phosphate or phosphite group is added to the 5'-hydroxyl group. The noted antisense references describe protocols for such synthesis. We prefer to utilize a modification of the procedure described in Ogilvie, K. K. et al, "The Use of Silyl Groups in Protecting the Hydroxyl Functions of Ribonucleosides" *Tethrahedran Letters*. 33:2861–2863 (1974) whereby silyl imidazole is used as a silyating agent; Ogilvie reports that a silylation reaction is specific for the 5' hydroxyl group of ribonucleosides. Once the 5'-hydroxyl group is protected, a "temporary" protecting group, most preferably DMT, can be added to the 3'-hydroxyl group. The skilled artisan is credited with the ability to discern alternative methods for obtaining reverse phosphoramidites.

Exemplary embodiments of the enzymatic processes of the present invention are particularly directed to the exponential amplification of double-stranded DNA (or DNA-RNA hybrids), although amplification of RNA and single stranded DNA are equally viable. Schematic representations of particularly preferred target sequence amplification protocols are depicted in FIGS. 1, 2 and 3. Schematic representatives of solid-phase amplification protocols are depicted in FIG. 4. In FIG. 1, the target sequence is double-stranded and of sufficient definition such that an ILO can be generated for hybridization to the strands of the target; in FIG. 2 the target sequence may comprise a point mutation such that a 3' ILO and a 5'-ILO are utilized for detection and amplification of the non-mutated sequence; in FIG. 3, a "gap" exists within the target sequence; in FIG. 4, an ILO is attached to a solid support via avidin, where the inverse internucleotide linkage comprises a biotin moiety. The disclosed ILOs are also useful in processes such as Single Stranded Conformational Polymorphism; exemplary systems which can be utilized for SSCP analysis include the PhastSystem™ (Pharmacia). Additionally, single stranded DNA binding protein (see 13(2) Biotechniques 188 (1992)) can be utilized in conjunction with the disclosed ILOs.

For the following portion of the disclosure, certain preferred embodiments of the invention are disclosed. It is to be understood, however, that these preferred embodiments are exemplary, and not limiting; those in the art are credited with the ability to utilize this disclosure in other enzymatic processes.

A. SINGLE 3'-ILO FOR USE IN EXPONENTIAL AMPLIFICATION

An embodiment of the invention where a single set of 3'-ILO molecules are utilized for the exponential amplification of double-stranded DNA is schematically set forth in FIG. 1. Upon hybridization, the ILO moiety, under appropriate conditions, elongates along the target strand (FIG. 1B) such that upon termination of the elongation and denaturation of the target:elongated 3'-ILO, four products exists: the two original strands, and two elongated ILO amplicons (FIG. 1C). Thereafter, the ILO amplicons can serve as the target sequence(s) in subsequent cycles (FIG. 1D–F). FIG. 1D provides the route for exponential amplification using the ILO product. As noted above, depending upon the length of the ILO and the target sequence, one, or both, of the avenues set forth in FIGS. 1E and 1F can take place: FIG. 1E represents self-priming of the ILO amplicon resulting in a circular double-stranded ILO amplicon; FIG. 1F represents elongation of ILO amplicon.

1. Nucleic Acid Target Sequences

The disclosed process can be utilized to produce exponential quantities of at least one targeted nucleic acid sequence. Sufficient detail regarding at least two regions of the target sequence is necessary such that an ILO can be generated which will hybridize thereto.

Any source of nucleic acid can be utilized as the source of the target nucleic acid sequence; the nucleic acid sequence can be in purified or non-purified form, and these choices are principally dependent upon the needs of the investigator coupled with the objectives of the amplification. For example, for clinical evaluations, it may be impractical to purify the target sequence to complete isolation; however, to the degree that the sample is not purified, the possibility of spurious amplification, leading to potential false-positive results, may increase. With a given nucleic acid ligase or polymerase and a sample of nucleic acids of given complexity, it is well within the ability of those of ordinary skill in the art to readily adjust or determine: stringency conditions; lengths of the ILO and the regions of the ILO; defined length of target sequence; annealing temperature of the ILO, in order to maintain the activity of the ligase and polymerase while at the same time maintaining the probability of spurious amplification to an acceptably low level.

The disclosed process may utilize either single stranded or double-stranded DNA or RNA as the target; additionally, DNA-RNA hybrids (which contain one strand of each) may be utilized. Mixtures comprising any of the foregoing may be utilized.

The target sequence to be examined can be obtained from any source, such as DNA or RNA isolated from bacteria, viruses, yeast and organisms such as plants or animals, from plasmid such as pBR322 and M13, from closed DNA or RNA. Techniques for accomplishing these tasks are considered to be within the purview of the skilled artisan. DNA may also be extracted from cells grown in tissue culture; see, for example, Maniatis et al; *Molecular Cloning, A Laboratory Manual* (New York: Cold Spring Harbor Laboratory; 1982) (hereinafter "Maniatis"), pp. 280–281.

Target nucleic acid sequences derived from clinical samples (e.g., skin scrapes, whole blood, serum, plasma, semen, tears, vaginal swabs, etc.) may be prepared by a variety of techniques which are available to the skilled artisan. Typically, a primary goal of these techniques is to purify the nucleic acids to a sufficient degree such that extraneous materials which might otherwise interfere with amplification of the nucleic acids are removed. For, e.g., a serum sample, preparation of the nucleic acids generally can comprise the following steps: incubate the serum for 1 hr. at 70° C. with proteinase K (Boehringer Mannheim) at 2.5 mg/ml in 25 mMMOPS (pH 6.5), 2.5 mM EDTA and 0.5% SDS. This is followed by the following extractions: phenol extraction and ether extraction. This is followed by ethanol precipitation. see, e.g., a Larzul, et al. *J. Heptol.* 5:199–204 (1987). As noted, other protocols and techniques are readily available for such purification.

2. 3'-ILO Preparation

Preferably, the ILO is prepared as disclosed above. The regions of hybridization of the ILO must be of sufficient length to allow for stable hybridization to the target sequence(s). Therefore, the length of the ILO can vary from as little as about four nucleotides to as many as hundreds of nucleotides. Additionally, the regions or other side of the 5'-5' internucleotide linkage can be of equivalent or different lengths such that if, for example, the length of the ILO was 100 bases, the 3'-5' region of the ILO could be 25 bases, such that the 5'-3' region of the ILO is 75 bases, respectively. It is preferred that the lengths of these regions be substantially identical. Those skilled in the art are readily credited with the ability to select lengths for the ILO that allow for hybridization to the target which, in turn, allows for enzymatic elongation of the ILO along the target.

Preparation of the ILO is preferably conducted such that the solid-support:3'-5' portion is generated using the protocol described in Beaucage, S. et al, *Tetrahedron Letters* 22:1859–1862 (1981) on a first automated instrument. This is then, most preferably, followed by transfer of the reaction column comprising this portion of the ILO to a second instrument, whereby reverse phosphoramidites are utilized to generate the second portion of the ILO using, for example, the protocol described in Ogilvie, K.K. et al. *Tetrahedron Letters* 33:2861:2863 (1974). Thereafter, cleavage and deprotection of the ILO is preferably accomplished using standard, well known techniques.

3. Strand Separation/Denaturation

Strand separation can be accomplished using any suitable denaturing method; these include utilization of physical, chemical or enzymatic means. A physical method of strand separation involves heating the nucleic acid until it is completely denatured; heat denaturation typically involves utilization of temperatures ranging from about 80° C. to about 105° C. (preferably about 95° C.) for between about 1 to about 10 minutes (preferably about 4–5 minutes). An additional physical method of strand separation involves altering the pH of the medium in which the double strands are located; pH denaturation typically involves utilization of a pH range of from about pH 11 to about pH 14 for between about 1 second to about 10 minutes. An enzymatic method of strand separation can rely upon utilization of enzymes referred to as helicases or the enzyme RecA, which has helicase activity and in the presence of ATP has been reported to denature double-stranded DNA. Reaction conditions suitable for separating the strands of nucleic acids with helicases are set forth in *Cold Spring Harbor Symposia on Quantitative Biology*, Vol. XLIII, "DNA Replication and Recombination (New York: Cold Spring Harbor Laboratory, 1978), B. Kuhn et al., "DNA Helicases", pp. 63–67, which is incorporated herein by reference. When heat denaturation is utilized (as is preferred), enzymes utilized in the ILO protocol are most preferably thermostable enzymes.

4. Procedural Steps

Preferably, the ILO reaction takes place in a buffered aqueous solution, preferably having a pH of between about 6.0 and about 9.0. Preferably, the reaction buffer comprises various components which allow for the efficient and specific cycling of the ILO reaction. When the polymerase enzyme is Taq polymerase, a particularly preferred buffering solution is 20 mM tris hydroxymethyl amino methane hydrochloric acid ("TRIS—HCl"), pH 7.8. Additional materials are preferably added to the reaction buffer; these materials are selected such that the cycling of the reaction is at high efficiency (e.g., the greatest amount of product per target template, preferably greater than 2x, more preferably $x^y$, and most preferably about $x^2$, where x is the number of target templates available during each cycle, and Y is greater than 1.0 but less than about 2) and high specificity (i.e., the correctness of the fidelity of the ligase and polymerase enzymes, where "polymerase fidelity" is defined as the preference of the enzyme to catalytically incorporate the correct nucleotide and "ligase fidelity" is defined whereby ligase activity is limited to nick-closing activity, e.g., ligation of two complementary oligonucleotide moieties that are adjacent to each other when hybridized to a target sequence); processivity is maximized; catalytic stability of the enzyme(s) is maintained; and reaction stability (i.e. reaction components are maintained in solution; non-specific activity is decreased; adhesion of reaction components to the surface of the reaction vessel is minimized, etc.) is maintained. Other materials, such as preservatives and the like, can optionally be added to the reaction buffer. It is most preferred that double deionized water be utilized to achieve a desired final volume of the reaction buffer.

When heat denaturation is utilized (as is preferred), thermocyclers capable of providing a temperature controlled environment to the reaction vessel within a cyclical range of temperatures are preferably utilized. Exemplary is the Perkin Elmer 480™ thermal cycler.

The ILO moiety is preferably present such that there are at least two ILO molecules per double-strand of nucleic acid target sequence. Preferably, the ILO is preferably present in a concentration ranging from about 2.0 nanomolar(nM) to about 200 micromolar(uM); preferably from about 200 nM to about 10 uM; and most preferably about 2.0 uM. The optimum quantity of ILO used for each reaction also varies depending on the target concentration, enzyme concentration, number of amplification cycles which are performed. Optimum concentrations can be readily determined by those of ordinary skill in the art.

Generally, the stringency of conditions is dependent upon temperature, buffer(s) and related parameters; however, the temperature parameter is typically easiest to control and therefore is a preferred stringency parameter which when varied, can be utilized to optimize the performance of the ILO reaction. As noted, directly related to stringency mediated by temperature is oligonucleotide moiety length—thus, the stringency conditions can be readily optimized by those in the art in accordance with the objective of ensuring that hybridization of the ILO to the target allows for enzymatic elongation of the ILO.

The means for elongation of the ILO, preferably a polymerase enzyme in conjunction with deoxyribonucleotide triphosphates (i.e. dATP, dGTP, dCTP and dTTP) and/or ribonucleoside triphosphates (i.e., ATP, GTP, CTP and UTP), is present in the reaction vessel before, during or after the ILO is admixed with the target sequence. Most preferably, the polymerase enzyme is a thermostable polymerase enzyme. A most preferred additional step involves admixing the polymerase to the reaction vessel which already includes the target sequence, dNTPs, and ILO moieties.

In a particular preferred protocol, all of the reagents are admixed in a reaction vessel, the temperature of which is such that hybridization and enzymatic activity is substantially prevented. This can be readily accomplished by adding the reaction components to a vessel that is maintained at about 4° C.; at this temperature, most, if not all, of the enzymatic activity is substantially prevented.

A most preferred order of adding the reactant components is as follows: reaction buffer; target sequence; dNTPs; ILO; thermostable polymerase enzyme. Most preferably, the thermostable polymerase enzyme is added after a "hot start", i.e., a first "denaturation cycle" is utilized before the polymerase enzyme is added to the reaction vessel. As stated, most preferably, these components are maintained at approximately 4° C. until initiation of the amplification process is desired. The reaction components can be added to the reaction vessel manually or by means of a robotic, automated laboratory workstation capable of automatically adding a variety of reaction components to a reaction vessel(s). A particularly preferred robotic, automated laboratory workstation is the BIOMEK® 1000 (Beckman Instruments, Inc., Fullerton, Calif.).

After the reaction components are admixed, if, as is most preferred, the reaction vessel has been maintained at 4° C., the reaction vessel is subjected to a "hot start", i.e., the temperature is increased to about 95° C. for about 5 min., in order to completely denature the target sequence prior to initiation of the ILO reaction by the addition of polymerase enzyme. This is preferably followed by the amplification cycles. A cycle requires annealing of the ILO moiety to the target sequences, and denaturation therefrom. Thus, if denaturation is mediated by temperature (as is most preferred), the cycles are regulated by adjusting the temperature of the reaction vessel. If a non-thermostable enzymes are utilized, then as the temperature necessary to denature the strands is achieved, it is substantially possible for the enzymatic activity of the enzymes to be destroyed; thus, fresh enzyme must be added after each cycle. It is principally for this reason that thermostable enzymes are preferably utilized.

The temperature utilized within each cycle is principally dependent upon the annealing temperature of the ILO moiety; the skilled artisan is readily credited with the ability to optimize the time and temperatures utilized in each cycle. For ILO moieties between about 6 to about 10 bases in length, the annealing temperature thereof is about 40° C.; at this temperature, heat-sensitive (i.e. non-thermostable) enzymes are active. However, as the length of the moieties increase, the annealing temperature increases, thus necessitating the use of thermostable enzymes or the addition of heat-sensitive enzymes after each cycle.

If other means of denaturation are utilized, such as physical means, enzymatic means, pH adjustment, or chemical means, the skilled artisan will appreciate that the means must be compatible with the reaction components. Optimization of such means with the components necessary to conduct the ILO process are considered to be within the purview of the skilled artisan.

The number of cycles is principally dependent upon the needs of the investigator. When the number of target copies available is low (i.e. less than about 1,000) the number of cycles can range from 10 to 40, preferably between 20 to 40, and most preferably about 40; when the number of target copies available is high (i.e. greater than 1,000) the number of cycles can be the same as above, but detectable results can be achieved with fewer cycles. Cycles in excess of 40 can be utilized. One quasi-limitation on the number of cycles is the amount of ILO molecules, dNTPs and enzyme utilized. After increasing cycles, these components will eventually be depleted such that additional cycles will not lead to additional amplification. Thus, as the desired number of cycles increases, it is preferred that the relative amounts of ILO molecules, dNTPs and enzymes increase; optimization thereof vis-a-vis the desired number of cycles, is considered to be within the skill of those in the art.

After the appropriate number of cycles is performed, the reaction may be stopped. An efficient manner is to inactivate the enzyme and this can, most preferably, be accomplished by lowering the temperature of the reaction vessel to 4° C. However, other approaches can be utilized, e.g., EDTA and a urea "stop" solution. Additionally, the enzymes can be chemically inactivated using methods known to those in the art, or the components can be separated: on, e.g., Sephadex™ columns; by filtration; by centrifugation; or by gel electrophoresis. Most preferably, the reaction is terminated by utilization of temperature.

A potentially fatal problem associated with any amplification protocol is contamination; this problem is particularly acute when the amplification protocol is being utilized for diagnostic purposes. For example, even modest contamination from one reaction vessel can lead to erroneous positive results, i.e., a desired target, which is present in first vessel but not in a second vessel, may be accidently transferred from the first vessel to the second vessel—thus, the second vessel will evidence amplification of the desired target when, in fact, that target was not originally present in the second vessel. Various approaches for substantially reducing the possibility of such contamination have been proffered. One such approach involves utilization of the enzyme uracil-N-glycosylase ("UNG"). UNG degrades uracil such that oligonucleotides comprising uracil, in the presence of UNG, are effectively degraded. Additionally, UNG can be inactivated with heat (i.e., about 80° C.). Thus, when concerns regarding contamination are attenuated, a preferred solution is to replace dTTP with UTP in the reaction mixture, such that the amplified products incorporate uracil in lieu of thymidine. After amplification of the target in the first vessel, UNG is added to the second vessel; if any amplified product from the first vessel has contaminated the second, the UNG will effectively degrade the contaminant. Thereafter, the second vessel is "hot-started" by heating the vessel to about 80° C., thereby inactivating the UNG. Thereafter, the dNTPs and/or enzymes can be added to the second reaction vessel for initiation of the ILO protocol.

5. ILO Labelling

Labelling of the ILO is discretionary and principally dependent upon the needs of the investigator. Preferably, the label is one that is capable of being readily manipulated and amenable to efficient detection. Additionally, the dNTPs can be labelled.

Approaches involving directly detectable labels include utilization of, e.g., dNTPs labelled with radioactive labels such as $^{32}P$, $^{35}S$, or $^{125}I$ which are incorporated into the ILO moiety or which are utilized vis-a-vis enzymatic elongation of the ILO moiety. However, when the latter approach is utilized, separation of the incorporated from the unincorporated labelled dNTPs is required.

Approaches for direct labelling of the ILO can be adapted from methodologies for labelling of oligonucleotides, which are well known in the art. A particularly preferred approach is the "end-labelling" approach whereby T4 polynucleotide kinase is used to introduce a 5'-end label by the transfer of the γ-phosphate from a ribonucleoside 5'-triphosphate donor (typically [γ-$^{32}P$]ATP) to the 5'-hydroxyl a 5'-ILO. See, e.g., Richardson, C. C., *The Enzymes*, Vol. XIV, Nucleic Acids Part A, Ed. Boyer, P. D. Acad. Press, p. 299, 1981. Alternatively, terminal deoxynucleotidyl transferase can be utilized to add a series of supplied deoxynucleotides onto the 3'-ends of the ILO; single nucleotide labelling is possible using, e.g., [α$^{32}$]deoxy NTP. See, e.g. Bollum, F. J. *The Enzymes*, Vol. X, Ed. Boyer, P. D. Acad. Press, 1974; Yousaf, S. I., et al *Gene* 27:309 (1984); and Wahl, G. M. et al *PNAS USA* 76:3683–3687 (1979). Labelled di-deoxyNTPs, e.g., [α$^{32}P$]ddATP, can also be utilized.

Alternatively, non-radioactively labelled ILO, such as hapten labelled ILO, are viable. See, e.g., WIPO Publication No. WO 91/19729 "Nucleic Acid Probes and Protein Probes" Adams, C. W. Publication Date of Dec. 26, 1991, which is incorporated herein by reference. A detection scheme involving such hapten-labels includes utilization of antibodies to the hapten, the antibodies being labelled.

A similar approach involves utilization of biotin and avidin, or the derivatives thereof. For example, biotin-11-dUTP can be utilized in lieu of dTTP, or biotin-14-dATP in lieu of dATP; labelled avidin, or the derivatives thereof, can then be utilized for detection. See, generally, Langer, P. R. et al, *PNAS USA* 78:6633–6637 (1981), which is incorporated herein by reference. Biotinylated phosphoramidites can also be utilized. See, e.g., Misiura, K. et al. *Nucl. Acids. Res.* 18:4345–4354 (1990), which is incorporated herein by reference. Such phosphoramidites allows for precise incorporation thereof at desired locations along the growing oligonucleotide moiety during the synthesis thereof.

Additionally, fluorescein-11-dUTP (see Simmonds, A. C. et al *Clin. Chem.* 37:1527–1528 (1991), incorporated herein by reference) and digoxigenin-11 dUTP (see Muhlegger, K. et al. *Nucleosides & Nucleotides* 8:1161–1163 (1989), incorporated herein by reference) can be utilized as labels.

Chemiluminescent substrates are also viable as labels. For example, horseradish peroxidase ("HRP") and alkaline phosphatase ("AP"), both of which can be directly cross-linked to nucleic acids (see, Renz, M. and Kurz, C. *Nucl. Acids Res.* 12:3435–3444 (1964), incorporated herein by reference) can be utilized as enzyme labels. Luminal, a substrate for HRP, and substituted dioxetanes, substrates for AP, can be utilized as chemiluminescent substrates. Exemplary of the HRP labelling protocol is the ECL system available from Amersham (Arlington Heights, Ill., USA).

Processes for labelling single stranded oligonucleotides, and labelled oligonucleotides, are also described in U.S. Pat. No. 4,948,882. The information described therein is also amenable for the disclosed ILO protocols.

In a research environment, where target amplification is not always performed on a continuing basis, utilization of radioactive labels may be preferred. In a non-research environment, e.g., in a clinical setting, such labels may not be preferred due to the disposal problem and allied risks associated with continued exposure to radioactive labels. Thus, non-radioactive labels may be preferred in these settings. Thus, the foregoing should not be construed as limiting, but rather as exemplary.

6. Detection of Amplified Product

Detection of the amplified product is primarily dependent upon the label(s) utilized; alternatively, MIAS, because of their inherent concatamerization, can create "scatter centers" amenable to detection, in the amplification reaction vessel, via nephelometric or turbidimetric protocols. I.e., direct detection of an amplification reaction after the amplification process. The skilled artisan is credited with the ability to select an appropriate detection protocol vis-a-vis the selected label.

By way of example, and not limitation, when radioactive labels are utilized, it is preferred that the amplified product and reaction components from the reaction vessel be subjected to some form of separating technique before detection, preferably "slab" gel electrophoresis; thereafter, x-ray sensitive film can be placed upon the separating medium whereby exposure thereof via the radioactive label evidences whether or not product amplification has occurred. Alternatively, the amplified products can be separated from the reaction components and radioactive counts can be measured using instruments adapted or designed for such measurements.

Non-radioactive labels can be visually identified or detected with instruments designed for such purposes. For example, if the label is an enzyme such as HRP and the substrate is a chromogenic material, the introduction of the substrate to the label can result in a color change, whereby the color provides evidence of the amplified product. Haptenic labels can be detected using anti-hapten antibodies having a detectable label(s) conjugated thereto.

For indirectly detectable labels, such as biotin, detection can be accomplished using avidin (or derivatives thereof) having a detectable label(s) conjugated thereto, or by capture and separation from the reaction admixture.

A further means for detection of amplified product includes utilization of nucleic acid probes which are complementary to the amplified product. For this type of detection, labelling of the oligonucleotide moieties is not necessary. If the target is present, amplification thereof will result in sufficient amounts of the target such that labelled nucleic acid probes can be used for detection. Single probes comprising directly or indirectly detectable labels can be utilized, or multiple probes comprising a directly or indirectly detectable label and capture moieties can be utilized. See, for example, U.S. Ser. No. 07/576,137 "Solution Phase Nucleic Acid Hybridization and Solid Phase Capture For Detection of Target Nucleic Acid, and Kit Therefore," which is incorporated herein by reference.

B. SINGLE 3'-ILO AND SINGLE 5'-ILO FOR USE IN DETERMINATION AND EXPONENTIAL AMPLIFICATION OF REGIONS OF MUTATION

An embodiment of the invention whereby amplification detection of a point mutation along a target sequence is schematically represented in FIG. 2A. In this embodiment, sufficient sequence information at the point of mutation(s) is known such that complementary ILO molecules can be generated.

With reference to FIG. 2A, the indicational arrow is directed to the region of a putative point mutation; for example, AAACGGGT would represent the correct sequence such that AAACAGGT would provide a point mutation, AAACGT would provide a deletion, etc. If the ILO molecules are designed to hybridize to the correct wild-type sequence, then, if a mutation is present, hybridization leading to enzymatic ligation of the ILO moieties intentionally should not result.

As will be appreciated, because of the requirement of ligation at the point where the ILO moieties hybridize to the target, one ILO must be a 3'-ILO (two 3' termini) while the other ILO must be 5'-ILO (two 5' termini). This will allow for ligation between a 3'-terminus of one ILO and a 5'-terminus of another ILO. For this reason, it is preferred that the 5'-ILO comprise a phosphate group at each 5'-terminus prior to initiation of the reaction protocol. Additionally, the sequence of each ILO is identical to cross-diagonal regions of the target sequences vis-a-vis the point of ligation. For example, and referencing FIG. 2A, the 3'-ILO comprises a sequence complementary to a region on STRAND A (TTTG portion of 3'-ILO complementary to AAAC region of STRAND A) and STRAND A COMPLEMENT (GGGT portion of 3'-ILO is complementary to CCCA region of STRAND A COMPLEMENT); because the target strands are by definition complementary, these sequences are identical to those represented on the complementary portions of the target sequences.

It is, of course, necessary to have access to the sequence of the region at a putative point of mutation; this allows for creation of the 3'-ILO and the 5'-ILO.

Again, referencing FIG. 2A, each complementary region of the 3'-ILO and the 5'-ILO is capable of hybridizing to the respective targets; under appropriate conditions, a ligation event follows, which joins the 3'-ILO to the 5'-ILO leading to two products which are available as targets during the next round.

1. Nucleic Acid Target Sequence

The information set forth in Section A.1 is applicable to this embodiment of the invention; as noted, information regarding the sequence at the region of nucleotide change leading to a mutation is necessary in order to generate the 3'-ILO and the 5'-ILO.

2. ILO Formation a) 3'-ILO Formation

The information set forth in Section A.2 is applicable to this embodiment of the invention.

b) 5'-ILO Formation

Essentially, a 5'-ILO is generated much in the same way that a 3'-ILO is generated. However, it is preferred that the reverse phosphoramidites be utilized for solid support attachment, i.e., solid support:rp5'-3' (where "rp" is reverse phosphoramidite). Thereafter, the reaction chamber can be removed from a first synthesizer and placed onto one utilizing traditional phosphoramidites such that a 3'-3' Inverse Linkage is created.

Avoiding 3'-ILO/5'-ILO Hybridization

The 3'-ILO and 5'-ILO are complementary to each other; additionally, and as will be appreciated by those in the art, the amount of 3'-ILO and 5'-ILO added to the reaction vessel is typically in excess to target sequence in order to drive an ILO:target hybridization. This also has the potential effect of increasing the possibility of driving a 3'-ILO:5'-ILO hybridization. Thus, the ILO moieties may be synthesized such that this type of ILO:ILO hybridization is substantially prevented. This may be accomplished by placing an "interfering moiety" within the internucleotide linkage, i.e. a biotin molecule. Alternatively, a nucleotide within or near the Inverse Linkage region can be utilized. For example, using the 3'-ILO and 5'-ILO of FIG. 2A, additional bases that are not complementary to each other can be utilized; FIG. 2B provides a schematic representation of the procedure.

In FIG. 2B, the 3'-ILO comprises two bases which are identical to the base in STRAND A (GG); this, of course, prevents complementary base pairing at this portion of the ILO. The 5'-ILO comprises two bases which are identical to the bases on STRAND A COMPLEMENT (GG) which has the same effect. Accordingly, the GG (underlined) of the 5'-ILO interferes with hybridization of the 3'-ILO to the 5'-ILO, due to non-complementarity within the central region of the two ILO moieties. In this embodiment of the invention where the "interfering moiety" is a nucleotide base, it is preferred that the number of interfering bases represent less than about 10% of the number of bases of the ILO, more preferably less than about 5% of the bases of the ILO. For example with an ILO comprising a total of 50 bases having 25 bases on either side of the internucleotidic linkage, it is preferred that 25 of the bases on one region of the ILO be absolutely complementary to a target region and about 20–23 bases of the other region of the ILO being absolutely complementary to a target region, with between about 5 and 2 bases being non-complementary as indicated.

3. Strand Separation/Denaturation

The information set forth in Section A.3 is applicable to the embodiment of the invention.

4. Procedural Steps

The information set forth in Section A.4 is applicable to this embodiment of the invention with the following modification. By definition, this embodiment of the invention requires ligation of the 5'-ILO and the 3'-ILO such that in addition to polymerase and dNTPS, a ligase enzyme, most preferably a thermostable ligase enzyme, is utilized. Cyclical processing allows for the amplification of the ligation product, assuming, of course, that ligation of the 3'-ILO and 5'-ILO is viable vis-a-vis the target sequence.

5. ILO Labelling

The information set forth in Section A.5 is applicable to this embodiment of the invention.

6. Detection of Ligation Product

A plethora of detection schemes for detection of ligation product (if present) are available. We prefer to utilize a two-tier detection scheme whereby a biotin moiety is incorporated into e.g., the 3'-ILO, and e.g., a radioactive label is incorporated into the 5'-ILO. Following the reaction protocol, the reaction vessel can be introduced to avidin-coated solid support. This has the effect of removing substantially all of the 3'-ILO and, if present, the 3'-ILO:5'-ILO ligation products. Critically, substantially none of the radioactively labelled 5'-ILO will be present. As such, if the separated material has detectable radioactivity not attributed to "background," a conclusion to be drawn is that ligation of 3'-ILO to 5'-ILO occurred.

C. GAP BETWEEN 3'-ILO AND 5'-ILO

An embodiment of the invention where a 3'-ILO and a 5'-ILO are designed to hybridize to a target such that upon hybridization a gap exists between the 3'-ILO and 5'-ILO, and the amplification process related thereto, is schematically set forth in FIG. 3.

1. Nucleic Acid Target Sequences

The information set forth in Section A.1 is applicable to this embodiment of the invention. However, by definition, the information regarding the sequence between the gap need not be known. For example, the sequence of the gap can be unknown; what is necessary is that sufficient detail regarding portion(s) on either side of the gap must be known such that complementary 3'-ILO and 5'-ILO can be generated.

2. ILO Formation

The information set forth in Section B.3 is applicable to this embodiment of the invention.

3. Strand Separation/Denaturation

The information set forth in Section A.3 is applicable to this embodiment of the invention.

4. Procedural Steps

Because of the need to "fill-in" the gap, polymerase enzyme, dNTPs, and ligase enzyme are necessary for this embodiment of the invention. Thus, the information set forth in Sections A.4 and B.4 are applicable.

Because of the necessity of utilization of polymerase enzyme and dNTPs, the possibility of extension of 3'-ILO hybridized to target strand in the direction opposite to the gap ("non-fill-in") exists. In and of itself this may not be critical and optimizing cycle time to allow for "fill-in" extension while decreasing the extension of non-fill-in extension is viable. Another approach is possible if the information regarding the sequence of the gap is (a) known, and (b) comprises only three of the four bases. This allows for utilization of three dNTPs such that non-fill-in extension is limited.

For gaps exceeding about 200 nucleotides in length, it is preferred that the reaction time for each cycle be increased; preferably, each cycle should be greater than about 10 minutes, i.e. greater than about 12–15 minutes. The intent of such increase is to increase cycling efficiency.

5. ILO Labeling

The information set forth in Sections A.5 and B.5 is applicable to this embodiment of the invention.

6. Detection of Ligation Product

The information set forth in Sections A.6 and B.6 is applicable to this embodiment of the invention. Particularly preferred detection schemes involve utilization of nucleic acid probes which are complementary to one (or more) of the oligonucleotide moieties; this would allow for "pulling" amplicons from the reaction vessel, whereby sequencing thereof can be accomplished.

Diagnostic applications involving this embodiment of the invention provides the opportunity to utilize a variety of labelled probes directed to specific mutations that lead to one or more alleles. I.e., for a variety of mutations known to exist within a particular region of a gene, the 3'-ILO and 5'-ILO can be designed to flank this region; amplification of the target will then generate amplicons of undefined mutations. Specific probes directed to the known mutational sequences can then be utilized to screen the amplicons such that, depending on which probe hybridizes with the amplicons, identification of the mutation can be accomplished. Those skilled in the art are credited with the ability to optimize the conditions necessary for screening of amplified targets as delineated above.

D. SOLID PHASE ILO EXTENSION OF TARGET

The disclosed ILO molecules allow for solid phase ILO extension using target sequences; beneficially, detection of the extended target product is made more efficient with this approach. Reference will be made to FIG. 4, wherein the target sequences, solid support, and 3'-ILO molecule are provided. The intent of this reaction is to generate an enzymatic elongation of the insolubilized ILO using the target sequence as the template. For convenience, this embodiment focuses upon insolubilized streptavidin and a 3'-ILO comprising a biotin moiety located at the 5'-5' internucleotide linkage.

A principal objective of this embodiment is elongation of the ILO via the target sequence for analysis of the extended ILO. As will be appreciated, in the arena of genetic analysis, amplification of a gene or gene-region is most typically followed by "probing" of the amplification product with, e.g., Allele Specific Oligonucleotides ("ASO"). This can be accomplished by affixing the amplification product to a solid support and then probing the insolubilized product with several ASO ("dot blot" approach) or by screening insolubilized ASOs with the amplification product ("reverse dot blot" approach). As is evident, these previous approaches require numerous steps, each of which are cumbersome which increases the possibility of mistakes.

In order to avoid such problems, we have exploited the ILOs to allow for solid-phase target extension, i.e. the extension product is insolubilized ab initio such that after the reaction, the insolubilized reaction product can be probed directly with ASOs.

Referencing FIG. 4, a biotinylated 3'-ILO is presented whereby the biotin portion thereof is, most preferably, incorporated at the Inverse Linkage. Utilizing an avidin (or streptavidin) solid support, the biotin portion of the 3'-ILO will lead to insolubilization of the 3'-ILO such that a generally "Y" or "T" shaped structure is formed. This arrangement is preferred because the biotinylated (or equivalent) ILO can be readily generated and admixed with the avidin coated solid support.

Thereafter, sample comprising target sequence is admixed with the insolubilized 3'-ILO, polymerase enzyme and dNTPs as set forth in detail in Section A, supra. Following appropriate cycling, the 3' termini of the insolubilized 3'-ILO will be enzymatically elongated.

Thereafter, the insolubilized material (i.e. CPG or equivalent material) can be removed from the reaction vessel and probed with ASOs as described above. Our preferred solid support material for this embodiment of the invention is aminated polypropylene as disclosed in Coassin, P. et al., U.S. Ser. No. 07/971,100, now abandoned PCT Application Ser. No. PCT/US93/09294, entitled "Biopolymer Synthesis Utilizing Surface Activated Organic Polymers," which is incorporated fully herein by reference (hereinafter "Coassin et al.").

G. UTILIZATION OF ILO TO INCORPORATE "SEQUENCE OF INTEREST" INTO A TARGET SEQUENCE TO BE AMPLIFIED

Frequently, it is desirable to incorporate a sequence of interest into a target sequence; for example, it may be advantageous to incorporate a restriction enzyme site at a termini/terminus of an amplicon so that the amplicon can be readily incorporated into a sub-cloning vector which also includes the same restriction site. In order to accomplish this objective, a modified ILO is generated which, most preferably, incorporates the complementary section of a restriction site sequence at a region of the ILO near the Inverse Linkage, such that the regions of the ILO complementary to the target sequence are positioned at the termini of the ILO.

For example, if it is desirable to incorporate a Cla I site (5'-ATCGAT-3') and a Bam HI site (5'-GGATCC-3') into the ILO such that the amplified target incorporates these sites, the ILO could have the following sequence:

3' AACTTCCTAGGNNN-NNNATCGATATTATCG 3'
       Bam HI           Cla I (Spacing bases, "N", may be required depending upon the enzymes selected. The number of spacing bases utilized, if any, will depend upon the enzyme utilized. This number can be determined by the skilled artisan.) As will be appreciated, upon amplification, the resulting ILO products will comprise both the Bam HI and Cla I sites. Thereafter, by digesting the ILO product with the respective restriction enzymes, the ILO product will be cut at these sites, thus producing "sticky ends" amenable to insertion into, e.g., sub-cloning vectors which have corresponding "sticky ends."

F. CUTTING OF CIRCULAR DOUBLE-STRANDED ILO AMPLICON TO GENERATE "NATURAL" DNA

Figure 5:
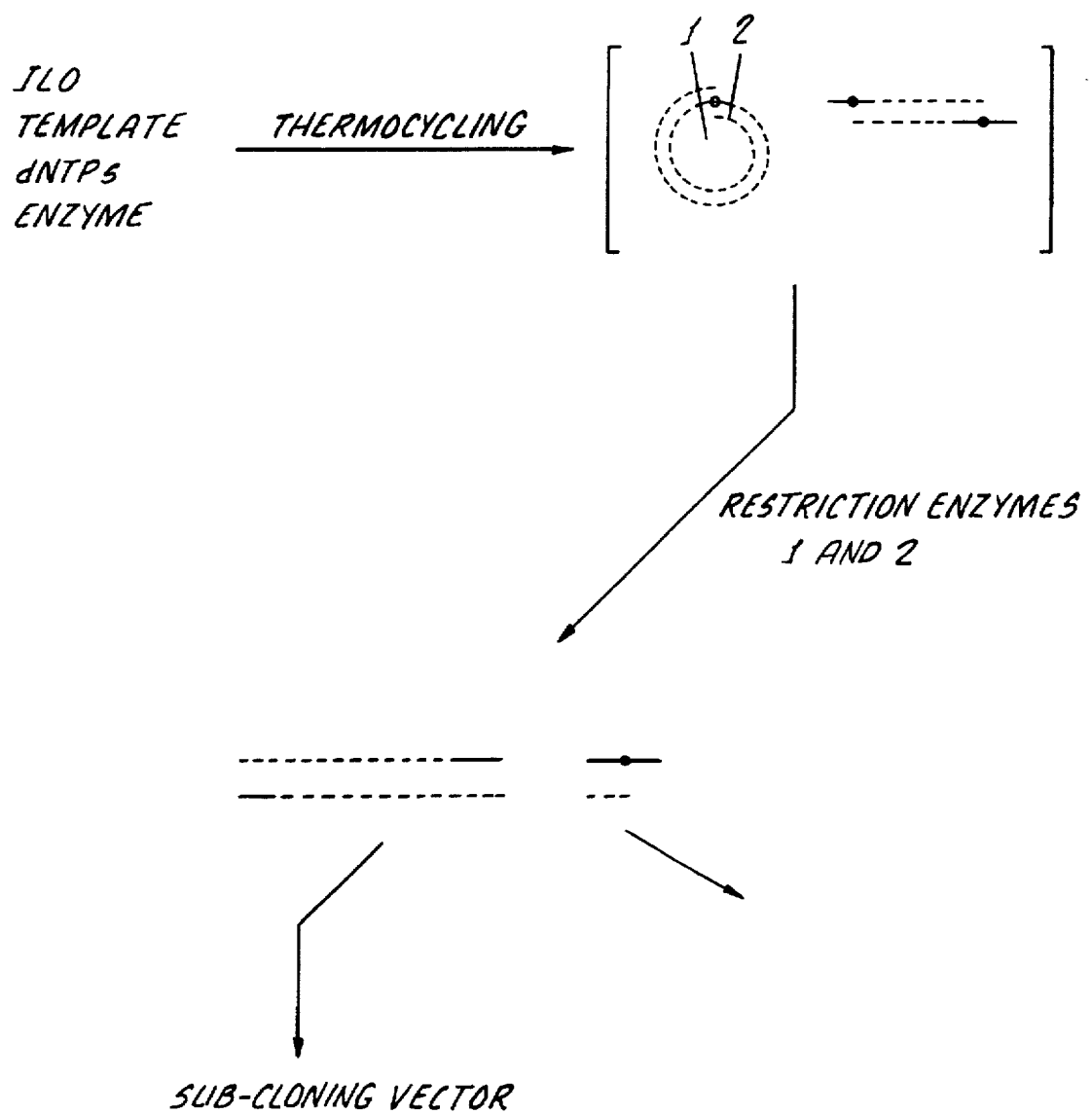
FIG. 5 is a schematic representation of the production of circular double-stranded ILO amplicon comprising two sites amenable to cutting with restriction enzyme to produce double-stranded "natural" DNA which can be inserted into an expression vector.

FIG. 5 provides a schematic representation of the generation of "natural" DNA from Circular Double-Stranded ILO amplicons. The objective of this protocol is to amplify a target sequence such that the resulting Circular Double-Stranded ILO amplicon comprises at least two restriction enzyme sites such that the Circular Double-Stranded ILO amplicon can be "cut" at these sites to generate natural double-stranded DNA. The natural double-stranded DNA can then be utilized for, e.g., insertion into appropriate sub-cloning vectors.

Most preferably, the restriction enzyme sites are incorporated into the ILO as set forth above in Section E.

G. MANIPULATION OF ILO AMPLICONS FOR "PURIFICATION" THEREOF

Figure 6:
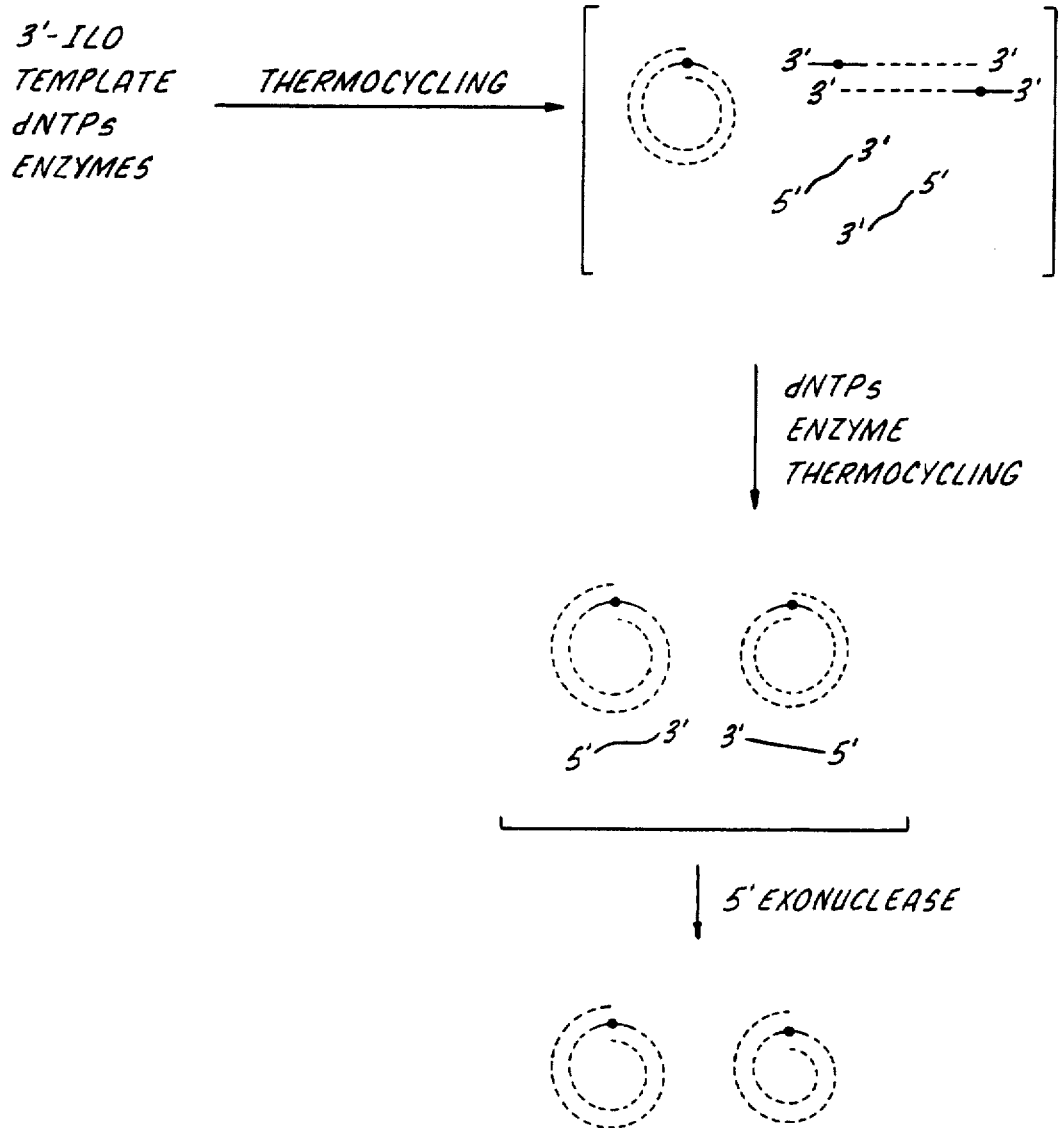
FIG. 6 is a schematic representation of the conversion of ILO amplicons into the circular form, and the purification of the reaction mixture.

As will be set forth in detail in the Examples to follow, ILO amplicons are amenable to self priming, i.e., in the presence of dNTPs and polymerase enzyme, the ILO amplicons can be "converted" into Circular Double-Stranded ILO amplicons. As will be further set forth in the Examples, Circular Double-Stranded ILO amplicons generated from 3'-ILOs, due to the conformational nature thereof, are more resistant to digestion by 5'exonuclease than 3'-ILO amplicons. A schematic representation of this approach is depicted in FIG. 6.

Following conversion of substantially all of the ILO amplicons into Circular Double-Stranded ILO amplicons, the admixture can be subjected to 5' exonuclease; we have determined that the most prevelant detectable product remaining in this admixture is the Circular Double-Stranded ILO amplicon.

The exonuclease is preferably a 5' exonuclease when the ILO is a 3'-ILO. Preferred 5' exonuclease include bacteriophage Lambda exonuclease and T7 Gene 6 exonuclease.

EXAMPLES

The following examples, which are neither intended nor construed as limiting, are directed to a particularly preferred embodiment of the invention—amplification of a nucleic acid macromolecule using a single ILO molecule.

I. MATERIALS, METHODS, INSTRUMENTS, SPECIFIED INVERSE LINKED OLIGONUCLEOTIDES

A. Instruments

1) Oligonucleotide and ILO Synthesis

Synthesis of natural oligonucleotides and ILO was performed on Beckman Instruments, Inc. (Fullerton, Calif.) OLIGO 1000 automated DNA synthesizer using phosphoramidite-based chemistry protocol. Controlled pore glass was utilized for the solid support material. For convenience, ILO was prepared using two instruments: in the first OLIGO 1000 synthesizer, "traditional" phosphoramidites were utilized to generate the first portion of the ILO; the column was then transferred to a second instrument, which included reverse phosphoramidites to generate the second portion of ILO.

2) Capillary Gel Electrophoresis ("CGE")

Capillary electrophoretic analysis of ILO was performed on a Beckman Instruments, Inc. P/ACE™ 2000 high performance capillary electrophoresis system. A 27 cm, 100 μm i.d. column (Polymicro Technologies, Inc., Phoenix, Az.) was utilized; polymerized polyacrylamide gel column was prepared in-house using 9%T. Samples were loaded onto the columns via the electrokinetic injection method (7.5 kV; 3.0 sec.); separation was conducted at 300 v/cm tris-hydroxymethyl amino methane-borate was utilized as the running buffer. Absorbance detection was at $OD_{260\ nm}$ while sample concentration was at 1.00 D/ml 3) Thermal Cycler A Perkin Elmer Thermal Cycler 480™ was utilized. Additionally, a National Labnet Company Thermal Reactor Hybrid Cycler was also utilized. Manufacturer instructions were followed.

B. Commercially Available Protocols

1) Polymerase Chain Reaction ("PCR")

Amplification of nucleotides 7131 through 7630 of bacteriophage lambda target segment was accomplished following PCR protocols using a Perkin Elmer CetusGene-Amp™ DNA Amplification Reagent Kit with AmpliTag DNA Polymerase (Part No. N801-0055). Manufacturer instructions were followed.

The GeneAmp kit includes the following primers for amplification:

(a) Sense (SEQ ID NO 1)
    5'  G ATG AGT TCG TGT CCG TAC AAC TGG  3'     25

(b) Antisense (SEQ ID NO 2)
    5'  G GTT ATC GAA ATC AGC CAC AGC GCC  3'     25

2) Primer Biotinylation

Biotinylation at the Inverse Linkage region of ILO was accomplished using Biotin-ON™ phosphoramidite (Clonetech Laboratories, Inc., Palo Alto, Calif., Part No. 5191). Biotinylated ILOs were not purified prior to utilization. Manufacturer instructions were followed.

C . Reagents

1) OLIGO 1000 DNA Synthesizer: Phosphoramidites

Synthesis of oligonucleotides for the Inverse Linkage Oligonucleotides was accomplished using Reverse Phosphoramidites (infra) and Beckman Instruments, Inc. BINARY-PAK™ phosphoramidites (dACBz)—Part No. 337737, dC(Bz)—Part No. 337738, dG(cbu)—Part No. 337739, T—Part No. 337746); DNA Synthesis Reagent Kit (Oxidize—Part No. 337732, DEblock—Part No. 337733, Cap 1—Part No. 337734, Cap 2—Part No. 337735); Activate Reagent (Part No. 338284); and Cleavage and Deprotection Kit (Part No. 337742).

Synthesis was conducted using Bioran controlled pore glass (pore size: 1000 Å).

2) Reverse Phosphoramidites ("3'-DMT Protected")

Figure 7:
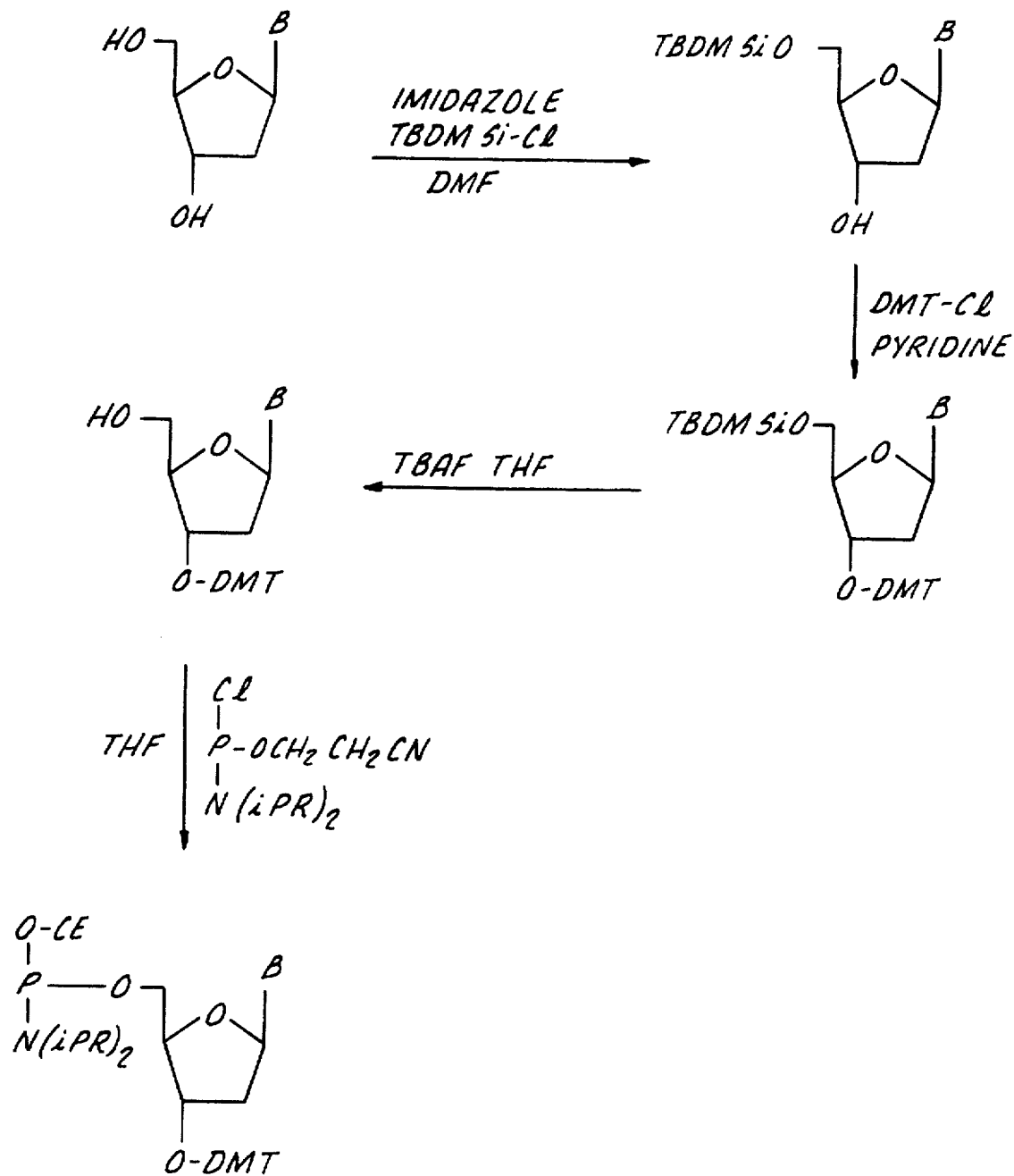
FIG. 7 is a schematic representation of the preferred synthesis route for reverse phosphoramidites.

3'-DMT protected deoxynucleosides were prepared following the schematic protocol set forth in FIG. 7. Briefly, the protocol utilizes t-butyldimethylsilyl ("TBDMS") as a transient protecting group for masking of the 5' OH group of the four (4) deoxynucleosides. Once protected, the conventional dimethoxytrityl ("DMT") protecting group is added to the 3'-OH group using conventional DMT-Cl/pyridine treatment. Cleavage of the 5'-TBDMS is then effected using fluoride ion to provide the required 3'-DMT nucleoside preparation of the reverse amidite is accomplished by treatment of the 3'-DMT nucleotide with the appropriate chlorocyanoethoxy phosphine.

The efficiency of the reaction is highly dependent on the maintenance of strictly anhydrous conditions. Solvents are most preferably of lowest water content available. With the silylation reaction, DMF should be distilled under vacuum to azeotrope off traces of water which may be resident in the nucleoside and solvent. Similarly, with the DMT reaction, pyridine should be evaporated in vacuo to remove traces of moisture. (Even with these precautions, it may be necessary to add additional equivalents of the TBDMS-imidazolide or DMT-Cl; see FIG. 7).

Because of the enhanced stability of the DMT group conjugated to the 3' region of the nucleoside, the 3'-DMT nucleosides are more stable in solution than the 5' isomers. The migration rates of the 3' DMT nucleosides on normal phase Thin Layer Chromatography ("TLC") are notably faster than the 5' DMT nucleosides. Additionally, 5' TBDMS ethers run more slowly than the 3' TBDMS ethers.

With the exception of T reverse phosporamidites, the remaining reverse phosphoramidites tend to be amorphous gums and chromatography is necessary for purification; the reverse phosphoramidites are glassy solids when pure.

(a) Materials and Methods

TBDM-SiCl, DMT-CL, and Chloro-cyanoethyloxy-diisoproylamino phosphine were obtained from Chem Impex (Woodale, Ill.) or Aldrich Chemicals (St. Louis, Mo.). TBAF/THF was obtained from Aldrich. Precursor nucleosides (dA(Bz), dC(Bz), dG(iBU) and T) were obtained from Chem Impex. TLC was performed on silica gel precoated on aluminum plates (E. Merck, Cat. No. 5534) using methanol (1% to 5%) in methylene chloride. TLC development. was by UV 254 nm, spraying with dilute perchloric acid to detect DMT, and charring with a hot air gun to detect deoxyribo-containing moieties.

Preparation of 3'-DMT-Thymidine-5'-Amidite is set forth below; the preparation of the other reverse phosphoramidites followed the same protocol and will be only briefly summarized. It is noted that the purines (A and G) react somewhat more slowly in the TBDMS and DMT reactions that the pyrimidines (T and C), but yielded reasonable results.

The compounds 5'-TBDMS-T-3'-OH ($C_{16}H_{28}N_2O_5Si$, MW: 356.5) was prepared as follows. TBDMSi-Chloride (2.04 g, 13.6 mmol) was dissolved in DMF (50 ml), followed by addition of imidazole (1.8 g, 27.2 mmol) with stirring at room temperature; this generated TBDMS-Imidazolide in situ. This solution was added to a stirred solution of thymidine (3.0 g, 12.4 mmol) in DMF. After one hour, the reaction was complete. The admixture was poured on ice to precipitate the product as a white solid; the product was filtered, admixed with methylene chloride, and partitioned two (2) time against water. Thereafter, the material was dried over $MgSOO_4$, and evaporated to yield a product. The product was then dissolved in ether:pet.-ether (1:1 ), filtered, and dried. Final product amount was 3.2 g (72%) and was referred to a "T-1".

5'-TBDMS-T-3'-ODMT ($C_{37}H_{46}N_2O_7Si$, MW: 658.8) was prepared as follows: 2.5 g (7 mmol) of T-1 was dissolved in pyridine (10 cc), and DMT-Cl (5.06 g, 15 mmol) was added with stirring. TLC indicated that the reaction was complete in 4 hrs. Methanol (5 cc) was added to quench excess DMT-Cl; thereafter, the solvent was evaporated, yielding final product "T-2" as an oil. (It is noted that additional equivalents of DMT-Cl are typically necessary to "drive" the reaction to completion; it is further noted that the excess DMT by-products do not interfere with the fluoride deprotection of the TBDMS group—accordingly, removal of such by-products is not considered essential.)

5'-HO-T-3'-ODMT ($C_{31}H_{32}N_2O_7$) MW: 544.58) was prepared as follows: T-2 was treated with 25 cc of 1.0M tetrabutylammonium fluoride ("TBAF") in THF. TLC indicated that the reaction was complete in four hours at room temperature. The solvent was evaporated and the residue dissolved in methylene chloride; thereafter, the material was applied to a silica gel column which was eluted with 0% to 2% methanol in methylene chloride. The resulting gum was dissolved in a small amount of methylene chloride and triturated with pet.-ether. This yielded a solid product which was filtered and dried under vacuo. Product weight was 2.1 g (82% based on TBDMS-T-OH) and was designated "T-3."

5'-amidite-T-3'-ODMT ("Reverse amidite:T") was prepared as follows: 1.5 g (2.72 mmol) T-3 was dissolved in 10 cc THF followed by addition thereto of 1.9 cc (10.88 mmol) diisopropylamine at room temperature. N,N-diisopropylamino-cyanoethoxy-chlorophosphine (1.2 cc, 5.4 mmol) was then added to the admixture, using magnetic stirring, while ensuring that the reaction was bathed in nitrogen. TLC (2% methanol/methylene chloride) indicated that the reaction was complete in 30 min; thereafter, the salts were filtered and THF evaporated at 30° C. under vacuo. The crude product was then re-dissolved in ethyl acetate (pre-treated with sodium carbonate, anhydrous), washed with water, followed by drying the organic layer over anhydrous $MgSO_4$ followed by evaporation under vacuo at 30° C. This yielded an oil which foamed under hi-vac. (An alternative approach to purification of the crude product is by $SiO_2$ column chromatography using ethyl acetate:pet.-ether (3:1) as the solvent system.)

Reverse amidites A, C and G were prepared following the same protocol, with the exception that thymidine was replaced with dA(Bz), dC(Bz), and dG(iBU) in the initial step.

3) Aminated Polypropylene: Avidin Solid Support

Aminated polypropylene threads (0.0254 cm diameter) were prepared as disclosed in Coassin et al.

D. Inverse Linkage Oligonucleotide ("ILO")

In a first series of experiments, ILOs utilized comprised the sequence of both the sense and antisense primers from the GeneAmp kit. Two comparative ILO experiments were conducted, whereby in one the ILO sequence was the opposite of that utilized in the other. This was effectuated in order to determine differences, if any, in the orientation of the ILO of the ILO products. ILO sequences for this experiment were as follows:

(1) A-180 (SEQ ID NO 3):

3'-GGT—CAA—CAT—GCC—TGT—GCT—TGA—GTA—G·    25
    GGT—TAT—CGA—AAT—CAG—CCA—CAG—CGC—C  3'    50

//
//

(2) A-181 (SEQ ID NO 4):

3' C—CGC—GAC—ACC—GAC—TAA—AGC—TAT—TGG·    25
    G—ATG—AGT—TCG—TGT—CCG—TAC—AAC—TGG  3'    50

ILO and PCR comparison primers were generated for studies involving amplification of amplicons from Exon 10 of the cystic fibrosis gene (wild type) generously provided by C. Thomas Caskey (Baylor Medical College, Houston, Tex.):

(1) A-240 (SEQ ID NO 5):

3'-CA—CGG-TCC—GTA—TTA-GGT—CCT—TTT—G·    24
    G—TTG—GCA—TGC—TTT—GAT—GAC—GCT—TC-3'    48

(2) SENSE (seq id no 6):

5'-GTT—TTC-CTG—GAT—TAT—GCC—TGG—CAC-3'    24

(3) Antisense (SEQ ID NO 7):

5' GTT—GGC—ATG—CTT—TGA—TGA—CGC—TTC-3'    24

For analysis of Bluescript pBKS+ phagemid (Stratagene, La Jolla, Calif.), including various inserts, ILO and PCR comparison primers were generated based upon the T3 and T7 promoters of the phagemid:

(1) A-189 (SEQ ID NO 8)

3'GAT—ATC—ACT—CAG—CAT—AA·ATT—AAC—CCT—CTC—ACT—AAA—G      36

//
//
//

(2) T3 Promoter, Sense (SEQ ID NO 9):

5'ATT—AAC—CCT—CTC—ACT—AAA—G-3'      19

(3) T7 Promoter, Antisense (SEQ ID NO 10):

5'ATT—ACG—ACT—CAC—TAT—AG-3'17

Biotinylated ILO was also prepared for solid-phase target elongation:

(1) A-206 (SEQ ID NO 11):

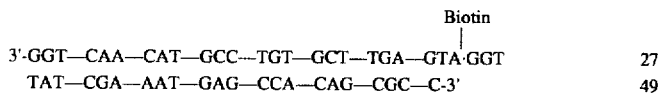

```
                                        Biotin
                                          |
         3'-GGT—CAA—CAT—GCC—TGT—GCT—TGA—GTA·GGT              27
             TAT—CGA—AAT—GAG—CCA—CAG—CGC—C-3'                49
```

II. EXAMPLE I: 3' ILO ENZYMATIC AMPLIFICATION

For the enzymatic amplification reaction, the PCR control was conducted following manufacturer instructions for amplification of the GeneAmp™ bacteriophage lambda target. For enzymatic amplification of this target sequence using the A-180 and A-181 3'-ILO molecules, this protocol was also followed, except that 100 picomole of A-180 was utilized, and 100 picomole of A-181 was utilized; these were added to a final volume of 100 microliters of reaction compounds for a final concentration for A-180 and A-181 of 1.0 micromolar each.

After the amplification reactions, substantially identical aliquots were obtained from each of the three reaction vessels and analyzed by slab gel electrophoresis (1.5% agarose gel). Results are presented in FIG. 8.

Figure 8:
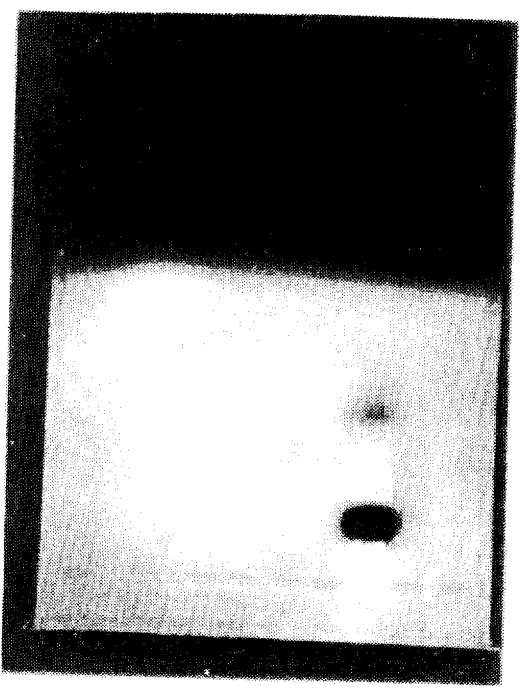
FIG. 8 is a photographic reproduction of the results of slab gel analysis of 3'-ILO enzymatic amplification of target sequence and PCR amplification of the same target sequence.

As the results of FIG. 8 indicate, exponential amplification of the target sequence was achieved using either the A-180 or A-181 3'-ILO and that, based upon the band intensities, the results are comparable to those achieved by the PCR control. It is further noted that the ILO amplicons are "longer" than the PCR amplification product—this difference is attributed to the additional reverse amidites or traditional amidites that extend from the ILO amplicons ("overhang"). Further note that the two ILO product lanes each consist of two distinct product bands; the lower product band comprises ILO amplicons while the higher band is attributed to the Circular Double-Stranded ILO amplicon; because 1.5% agarose was utilized, the resolution between these ILO products is not "extensive." However, two distinct bands do appear in the ILO product lanes.

III. EXAMPLE II: ILO AMPLICON SUB-TYPES

Target sequences of various lengths were inserted into the pBluescript phagemid; the inserts were amplified using PCR primers or ILO. These results are collectively presented in FIG. 9. For these results and under the slab gel electrophoretic conditions utilized, the stated "Expected size" is based upon the PCR amplicons; the ILO product runs more slowly due to either the overhang or the circular configuration.

Unlike the results of Example I, the reults of Example II were resolved on 5.0% agarose gel. As will be noticed, in the ILO product lanes, at least three distinct bands are resolved; two of these are resolved at about the same size, while one is resolved at a very different size. The slowest band is attributed to the Circular Double-Stranded ILO amplicon, as we will establish below. The "fastest" bands are attributed to ILO amplicons which have hybridized with each other in a double stranded fashion, with the "faster" of the two being two Partially Extended ILO amplicons hybridized in a double stranded fashion (including two "overhang portions), and the "slower" of the two being two Fully Extended ILO amplicons or one Partially Extended ILO amplicon and one Fully Extended ILO amplicon hybridized in a double stranded fashion.

(a) CF Exon 10: Expected size of 98 bp.

The portion of Exon 10 of the CF gene amplified was 98 bp in length ("CF amplicons"). The CF amplicons were sub-cloned into the phagemid as follows: CF amplicons were blunt ended using Klenow (see Maniatis) and ligated blunt ended CF amplicons were ligated into Sma I cut phagemid ("CF subclones").

Amplification conditions were identical for both ILO and PCR conditions, with the exception that 100 pmole of each PCR primer (SEQ ID NO 6 and 7) was utilized, and 200 pmole of ILO (SEQ ID NO 5) was utilized. Amplification was performed in 100 µl total volume using a Perkin-Elmer GeneAmp Kit in a Hybaid thermal cycler. One (1) µl of alkaline lysis plasmid mini-prep (~50 ng DNA) was used as a template. Thermocycling (40 cycles) conditions were: 95° C., 15 sec.; 60° C., 20 sec.; 72° C., 30 sec. Ten (10) µl of each reaction mixture was loaded onto separate lanes of a 5% acrylamide gel, followed by staining with ethidium bromide.

Figure 9:
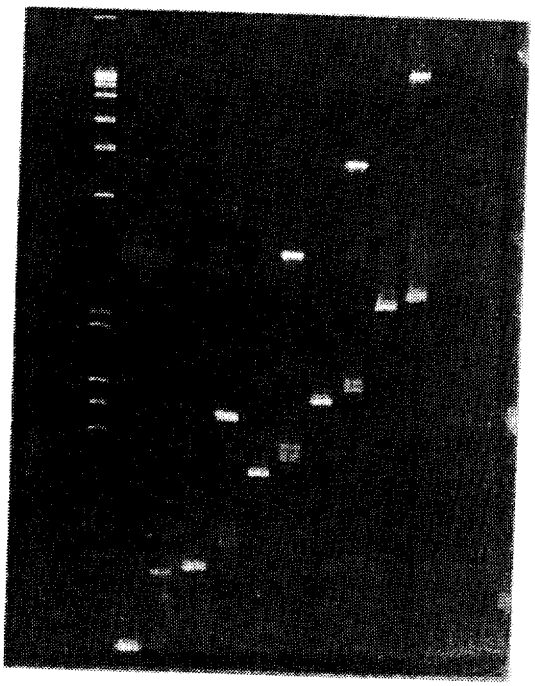
FIG. 9 is a photographic reproduction of, inter alia, the results of ILO amplification of targets of various lengths.

Lane 2 of FIG. 9 are the PCR amplicons; lane 3 are ILO amplicons. The size differential seen between lanes 2 and 3 indicates that substantially all of the ILO amplicon product is in the circular form; comparatively less of the ILO amplicons are present in lane 3. (Lane 1 of FIG. 9 is a 1 Kb ladder size marker, obtained from BRL, Bethesda, Md.).

(b) Polylinker from Phagemid: Expected size of 164 bp.

The polylinker from the phagemid was utilized as the target; the expected size of the resulting PCR amplicons was 164 bp. T3 and T7 promoter regions were utilized for PCR primers (SEQ ID NO 9 and 10) and ILO (SEQ ID NO 8). Conditions were as set forth in Example II(a), except that thermocycling (40 cycles) conditions were as follows: 95° C. 15 sec., 55° C., 20 sec , 72° C., 30 sec. for 40 cycles.

Lane 4 of FIG. 9 are PCR amplicons while lane 5 of are ILO product. As with Example II(a), substantially all of the product is Circular Double Stranded ILO amplicons, although the appearance of ILO amplicons is also evident.

(c) Polylinker+Exon 10: Expected Size of 262 bp

Exon 10 of the CF gene (98 bp) was subcloned as described above into the polylinker region of the phagemid (164 bp). Thus, the expected PCR amplicon size is 262 bp. Amplification conditions were as set forth in Example II(b). Lane 6 of FIG. 9 are PCR amplicons; Lane 7 are from the ILO amplification reaction.

As is evident, at this target size, the appearance of two distinct ILO sub-products is more pronounced, although the upper band (circular form) has a stronger staining intensity. Again, the ILO amplicons run "slower" that the PCR amplicons due to the inclusion of the 17 bp "overhang" attributed to the ILO moiety and the types of hybridization-product described above.

(d) Polylinker+Tandem Double Inset of Exon 10: Expected Size of 360 bp.

This target was substantially identical to that of Example II(c) except that a tandem double inset of Exon 10 (98 bp+98 bp) was inserted into the polylinker of the phagemide (164 bp) such that the expected PCR amplicons were 360 bp. Amplification was as in Example II (c). Lane 8 are PCR amplicons; Lane 9 are from the ILO amplification reaction.

As with Example II(c), two distinct ILO products are produced.

(e) Polylinker+subclone of Drosophila DNA: Expected size of 623 bp.

A PCR amplicon of a 466 bp subclone of Drosophila DNA (previously sequenced) was inserted between the Hind III and Eco RV sites of the polylinker portion of the phagemid (in so doing, approximately 17bp of the polylinker is lost, such that the expected PCR amplicons are 623 bp). Amplification was as set forth in Example II(c). Lane 10 are PCR amplicons; Lane 11 are from the ILO amplification reaction.

At this target length, both the ILO amplicons and the Circular Double-Stranded ILO amplicons are approximately equal in staining intensity.

Figure 10:
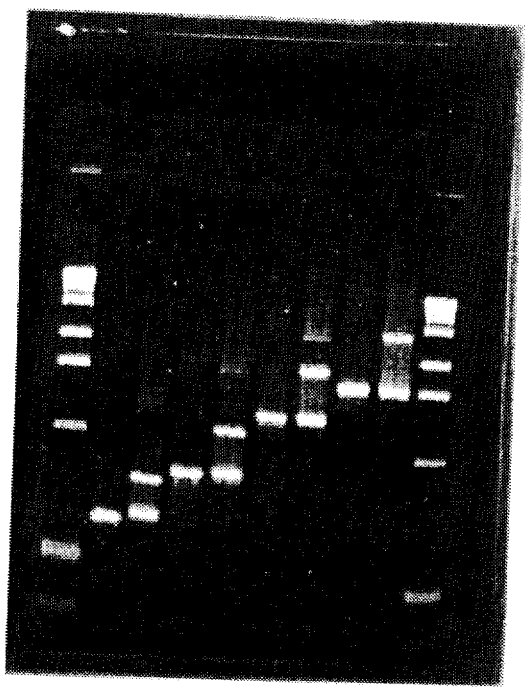
FIG. 10 is a photographic reproduction of, inter alia, the results of ILO amplification of targets of various lengths.

For Examples II(f)–(h), results are presented in FIG. 10; this was necessitated due to the target size and the need for utilization of 2% agarose gels as opposed to 5% acrylamide gel (i.e., agarose was required to resolve the larger sized amplicons of Examples II (f)–(h)). Lane 1 of FIG. 10 is the 1 Kb ladder size marker; lanes 2 and 3 are the same amplification products of Example II(e) (lane 2-PRC; lane 3-ILO); these are presented for comparative purposes. Amplification conditions and amounts of material analyzed were as set forth in Example II(e).

(f) Polylinker+subclone of Drosophila DNA: Expected size of 846 bp.

A PCR amplicon of a 724 bp subclone of Drosophila DNA was inserted between the Hind III and the Xba I sites of the polylinker of the phagemid (approximately 42 bp of the polylinker is lost in this process). Lane 4 of FIG. 10 are PCR amplicons; lane 5 is from the ILO amplification reaction.

(g) Polylinker+subclone of Drosophila DNA: Expected Size of 1285 bp.

A PCR amplicon of a 1152 subclone of Drosophila DNA was inserted between the Hind III and Bam HI sites of the polylinker of the phagemid (approximately 31 bp of the polylinker is lost in this process). Lane 6 of FIG. 10 are PCR amplicons; lane 7 is from the ILO amplification reaction.

(h) Polylinker+subclone of Drosophila DNA: Expected Size of 1665 bp

A PCR amplicon of a 1528 bp subclone of Drosophila DNA was inserted between the Hind III and Smal sites of the polylinker of the phagemid (approximately 37 bp of the polylinker is lost in this process). Lane 8 of FIG. 10 are PCR amplicons; Lane 9 is from the ILO amplification reaction.

The results of Example II, as evidenced by FIGS. 9 and 10, indicate that enzymatic amplification by ILO is viable across a wide range of target lengths (100 bp to 1.5 Kb). Additionally, for somewhat "smaller" targets (i.e. about 250 bp and less), substantially all of the ILO amplicons are in the circular form; thereafter, as the size of the target increases, the appearance of ILO amplicons begins—however, Circular Double-Stranded ILO amplicons are always formed throughout this target range, irrespective of target size.

IV. EXAMPLE III. DEFINITIVE ESTABLISHMENT OF CIRCULAR DOUBLE-STRANDED ILO AMPLICON

As noted throughout this document, we have postulated the formation of Circular Double-Stranded ILO amplicons. Evidentiary proof is best exemplified by subjecting what is presumptively Circular Double-Stranded ILO amplicons to a double-stranded restriction enzyme, with PCR amplicons serving as the control. Digesting PCR amplicons should result in two products via gel electrophoresis. Digesting Circular Double-Stranded ILO amplicon should result in a single band—because this product is, in actuality, "linear," but has double-stranded characteristics, cutting thereof should "release" or "un-hook" the product, resulting in a unitary product that should run at about the same size as PCR amplicons. This is schematically represented in FIG. 11.

Figure 12A:
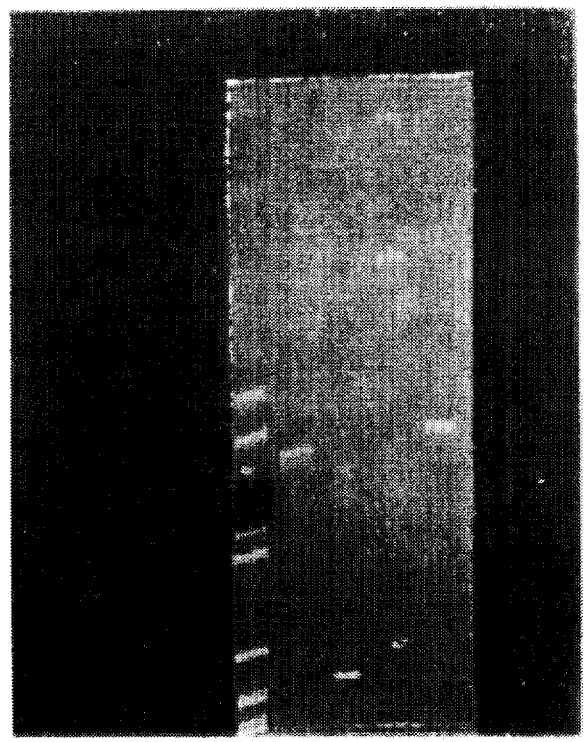
FIGS. 12a and 12b are photographic reproductions of, inter alia, the results of the effect of cutting Circular Double-Stranded ILO amplicon with a restriction enzyme.

10 µl of the PCR amplicons from Example II (b) (phagemid polylinker) was loaded onto 5% acrylamide gel and stained with ethidium bromide; results are presented in Lane 1 of FIG. 12a.

The phagemeid polyliner includes a Hind III site such that digesting the PCR amplicon with Hind III should result in fragment sizes of 97 and 67 bp. 50 µl of the PCR amplicon was desalted and separated from unused PCR primers using CHROMA SPIN+TE-100 columns (Clonetech); manufacturer instructions were followed. 10 µl of the desalted and separated PCR amplicons were then digested with 10 units of Hind III (Stratagene) in 30 µl of the buffer recommended by Stratagene for one hour, and the entire digest mixture was loaded into lane 2 of the gel of FIG. 12a. As expected, two bands appear at approximately 97 and 67 bp.

10 µl of the ILO reaction mixture from Example II(b) was loaded onto lane 3 of FIG. 12a; this is the putative Circular Double-Stranded ILO amplicon. 50 µl of this reaction mixture was treated with Hind III in the manner set forth above and the entire digest mixture was loaded into lane 4 of FIG. 12a. If this product is a circular double-stranded material, when cut it should evidence a single band at approximately 164 bp because cutting this circular product "linearizes" the product. The results from lane 4 evidence such a band. (Lane 5 of FIG. 12a is the 1 kb ladder size marker).

Figure 12B:
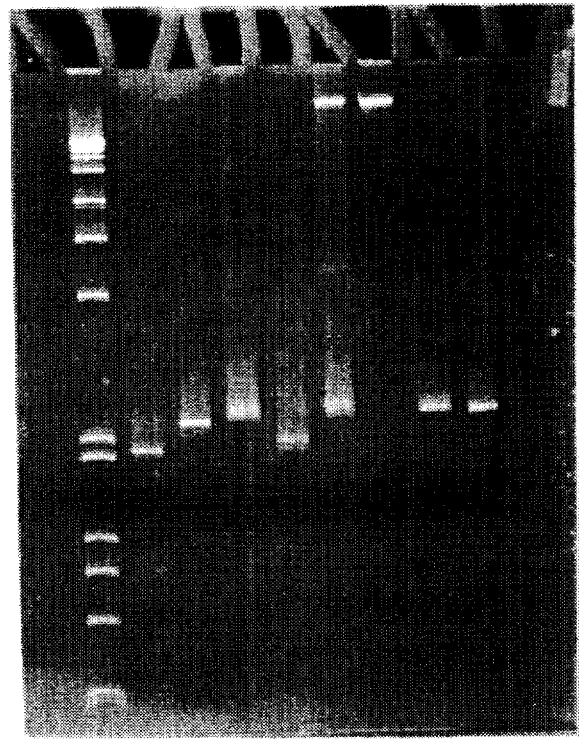

Repeating the conditions and protocol set forth in Example II(e), 10 uL of the resulting PCR amplicons were digested with Hind III as described above and the entire digest was loaded onto lane 2 of FIG. 12b (lane 1 of FIG. 11b is the 1 Kb ladder). When the PCR amplicons are digested, two bands should result, with one at approximately 500 bp, and the other at approximately 125 bp; in order to resolve the larger band for this Figure, the smaller bands were run off the gel and consequents, are not visible. Lane 2 evidences the larger band of the Hind II digested PCR amplicons located at about 500 bp. For comparative purposes, 10 ul of untreated PCR amplicons are presented in lane 3; these run at approximately 623 bp, as expected.

Lane 6 of FIG. 12(b) is an aliquot of ILO products which resulted from ILO amplification of the target sequence of Example II(e) following the same conditions and protocol of that Example. As expected, two distinct band regions appear, the lower being the ILO amplicons which run slightly slower than the PCR amplicons due to the overhang. The upper band is the circular form of the ILO product. The remainder of the ILO products were resolved on a 1.5% low melt agarose gel (results not shown); the two band regions were individually cut from the gel and the ILO products extracted by phenol extraction (see Maniatis). Lane 4 of FIG. 12b is an aliquot of the phenol extract lower band (ILO amplicons), and these are resolved at comparatively the same location as the lower band of lane 6. Digesting the ILO amplicons with Hind III should also result in two products akin to the digested PCR amplicons. 10 uL of the lower band (phenol extract) was digested with Hind II as described above, and the entire digest loaded onto lane 5 of FIG. 12b; the resolved band is slightly larger than the comparative PCR-digested band, due to the overhang of the ILO amplicon. Lane 7 is an aliquot of the phenol extract upper band (Circular Double-Stranded ILO amplicon), and these are resolved at comparatively the same location as the upper band of lane 6. 10 ul of the upper band phenol extract was also digested with Hind III as described above, and the entire digest was loaded onto lane 8 of FIG. 12b; as is evident, these run at about the same size as the PCR amplicons (for ease of comparision, the material of lane 3, i.e., un-digested PCR amplicons, were also run on lane 9 of FIG. 12b).

These reults indicate that ILO amplicons are linear in nature, while the Circular Double-Stranded ILO amplicons are circular in nature.

V. EXAMPLE IV. DEFINITIVE ESTABLISHMENT OF "OVERHANG"

While the results of Examples I and II lend credence to our explanation that the "slower" travelling ILO amplicons vis-a-vis PCR amplicons is due to the inclusion of the overhang on the ILO amplicons, we experimentally tested this proposition by subjecting ILO amplicons to Mung bean exonuclease, a single-stranded specifc exonuclease. ILO amplicons subjected to this exonuclease would be expected to be digested from the overhang back to a region where complementary double-stranded DNA begins such that the digested ILO amplicons would run substantially the same on the slab gel (5% acrylamide) as corresponding PCR amplicons.

The lower band from the ILO products of Example II(e) was segregated from the gel as described above and desalted as described above; for comparative purposes, the PCR amplicon band was similarly segregated and desalted. A 10 uL aliquot of ther ILO amplicons was admixed with 1 unit of Mung bean exonuclease and allowed to react for 30 min. at 37° C. Thereafter, substantially identical aliquots from the PCR and ILO segregated mixtures, and the digested ILO segregated mixture, were loaded onto lanes 1, 2 and 3 of a 5% acrylamide slab gel and electrophoresied as described, followed by staining as described; results are presented in FIG. 13.

Figure 13:
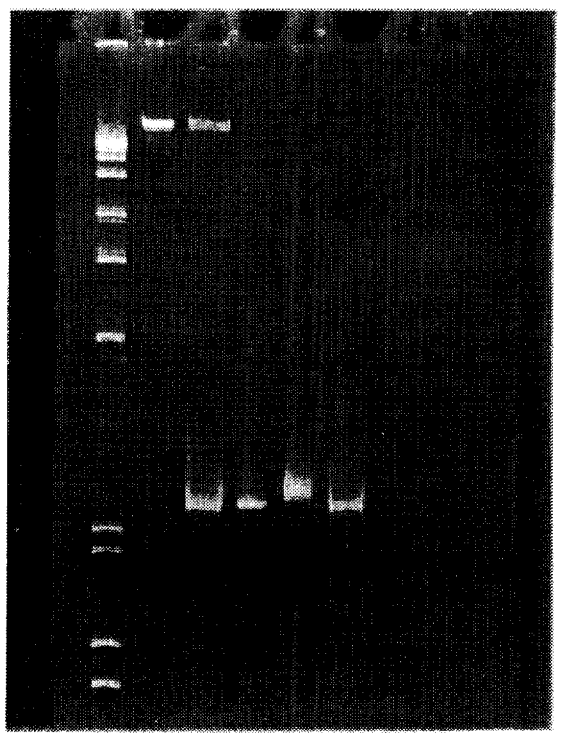
FIG. 13 is a photographic reproduction of, inter alia, subjecting ILO amplicons to Mung bean exonuclease.

As evident from the gel of FIG. 13 the ILO amplicons (lane 2) run slightly slower than the PCR amplicons (lane 1), due to the single-stranded overhang; once this overhang is digested, however, the digested ILO amplicons (lane 3) run substantially the same as the PCR amplicons.

Based upon the results of Example III, the presence of the overhang on the ILO amplicons facilitates a different traversal through the slab gel relative to PCR amplicons

VI. EXAMPLE V: ILO AMPLICON SELF-PRIMING

The ability of ILO amplicon to "self-prime," i.e., to serve as template for the generation of the Circular Double-Stranded ILO amplicon form, is a unique feature attributed to the ILO moiety—to our knowledge, no other amplification product, including PCR amplicons, can self-prime. Because of the ability of the ILO amplicons to self-prime, we can "drive" the amplification reaction such that substantially all of the resulting ILO amplification product is of the Circular Double-Stranded form. This allows us to purify the product using, in the case of 3'-ILO, a 5'-exonuclease, as disclosed previously, or to cut the resulting circular double-stranded ILO amplicons for, e.g., insertion into sub-cloning vectors.

Figure 14:
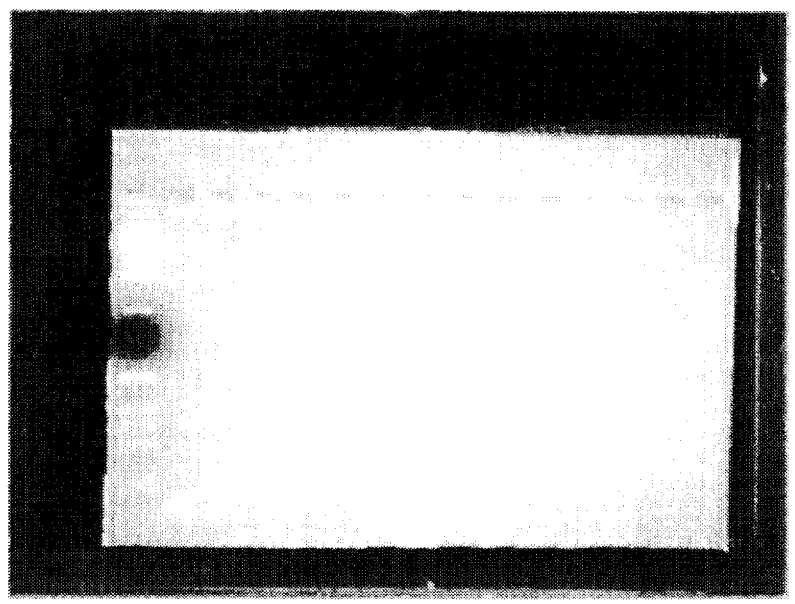
FIG. 14 is a photographic reproduction of, inter alia, the results of ILO amplicons subjected to "self priming" conditions.

Referring to FIG. 14, lane 1 is 10 uL of the ILO amplification product from Example II(c), (i.e., CF fragment subclone), where the upper band is Circular Double-Stranded ILO amplicon and and the lower band is ILO amplicons. As described in Example III, an aliquot of the reaction product was resolved on low melt agarose, and both band regions were segregated and desalted as described above; 30 uL of the desalted ILO product was added to the identical reaction components of Example II(c) (i.e., ILO, target, dNTPs, enzyme) and the admixture was thermocycled for 40 cycles as described in Example II(a). 30 uL of the resulting product was loaded onto lane 2 of the gel (due to the three-fold dilution, this is equivalent to the 10 uL loaded onto lane 1); based upon the comparative band intensities, more product was produced in the reaction for lane 2—this would be expected because the ILO product functions as target for additional product formation. Thereafter, 30 uL of the desalted ILO product were utilized in a reaction similar to Example II(c) except that no additional ILO was added to the mixture (i.e., the reaction components were desalted ILO product, dNTPs and enzyme). 30 uL of the resulting product was loaded onto lane 3 of the gel and resolved. As is evident, the strong band of lane 3 is resolved at subtantially the same region as that of the Circular Double-Stranded ILO amplicon of lane 1; because no ILO was utilized in this reaction, and because the lower band has, in effect, "disappeared," the postulated self-priming capability of the ILO amplicon has been established—the ILO amplicons, in a "target depleted" environment (i.e., dNTPs, enzyme, ILO amplicons) were capable of self-priming such that the ILO amplicons were transformed into the Circular Double-Stranded ILO amplicons.

Thus, we have, for the first time, demonstrated that an amplification product (ILO amplicon) can itself serve as a template to produce a different amplification product (Circular Double-Stranded ILO amplicon).

VII. EXAMPLE VI: EXONUCLEASE PURIFICATION

Following the conditions and protocol of Example II(b), 10 uL of the resulting PCR amplicons were loaded onto lane 4 of the gel of FIG. 15 (5% acrylamide); 10 uL of the ILO products were loaded onto lane 3. Lane 2 of FIG. 15 is a mixture of 5 uL of the PCR amplicons and 5 uL of the ILO products; the resulting bands are located, as expected, at substantially the same locations as the bands of lanes 3 and 4.

To a mixture of 5uL of the PCR amplicons and 5 uL of the ILO product was added 1 unit of Gene 6 exonuclease (USB); this exonuclease is 5' specific. The reaction proceeded for 1 hr. at 37° C. The entire mixture was loaded onto lane 1 of the gel of FIG. 15.

As is evident, the PCR amplicons are not present in lane 1, as would be expected. The principal remaining band of lane 1 corresponds to the Circular Double Stranded ILO amplicons. Using this purification approach, we can further distinguish the circular form of the ILO product from the ILO amplicons, and PCR amplicons.

VIII. EXAMPLE VII: SPECIFICITY OF ILO REACTION

In order to establish that the ILO is capable of selecting its target from a complex genomic background, we conducted the following experiment, with results being presented in FIG. 16 (lane 1 is the 1 Kb ladder).

Lanes 2 and 3 represent 10 uL each of the PCR amplicons and ILO products of Example II(b) (conditions and protocols conducted as described in Example II(b)); these are presented for comparative purposes.

Lanes 4 and 5 represent 10 uL each of the PCR and ILO products of Example II(b) (repeated as described above) with the exception that 0.5 ug of human DNA (Promega) was added to the reaction mixture to create the complex genomic background.

For the remaining portions of this Example, all conditions were identical to those which led to the products of lanes 4 and 5, except that the amount of template (i.e., the phagemid, where the polylinker portion thereof being the target sequence) was serially diluted. Template amount and corresponding lane of FIG. 16, are as follows:

| Template Amount | LANE | |
|---|---|---|
| | PCR | ILO |
| 1000 nanoliters | 4 | 5 |
| 100 nanoliters | 6 | 7 |
| 10 nanoliters | 8 | 9 |
| 1 Kb ladder | 10 | |
| 1 nanoliters | 11 | 12 |
| 0.1 nanoliters | 13 | 14 |
| 0.01 nanoliters | 15 | 16 |
| 0.001 nanoliters | 17 | 18 |

Based upon the results of Example VIII, the ILO is capable of specifically selecting and amplifying a target sequence over a wide range of target sequence concentrations intermixed with complex DNA.

IX. EXAMPLE VIII: SOLID PHASE 3' ILO TARGET ELONGATION

A-206 is a biotinylated 3'-ILO; the biotin molecule was provided at the internucleotidic junction via a biotinylated dATT phosphoramidite. Analysis of A206 by CZE (column: 27 cm; polyacrylamide gel, 9% T) evidence a single peak indicating production of a single major product (data not shown). Avidin, a protein, will not traverse a CZE capillary column. An aliquot of A-206 was admixed with avidin (labelled with FITC) in solution and an aliquot of this admixture was subjected to the aforementioned CZE conditions. No peak was observed, indicating that A-206 included a biotin moiety (data not shown); i.e., conjugation of the biotin portions of A-206 with avidin prevents traversal of the A-206:avidin conjugate through the capillary column.

Preparation of aminated polypropylene comprising avidin covalently attached thereto was accomplished as follows: succinate anhydride (0.10060 g) was dissolved in 10 ml of 500 µM NaAc, pH 5.55. 10 cm length of aminated polypropylene thread were soaked in the acetate buffer; after decanting of the buffer, 2 ml of the succinate anhydride was added to the thread and the reaction vessel was capped. The reaction proceeded for 24 hrs. at room temperature with end-over-end rotating of the vessel. The threads were then rinsed as follows: 2×2 ml acetate buffer; 2×2 ml water; 3×2 ml anhydrous IPA Iso-propropyl alcohol ("IPA"). Thereafter, 0.05671 g of 1-ethyl-3(-3 dimethyl aminopropyl) carbodiimide-HCl (Pierce #22980) in 15 ml anyhydrous IPA was prepared and 8 ml thereof was added to the threads. This reaction proceeded for 2 hrs. at room temperature with end-over-end rotation of the vessel. Threads were then rinsed with 2×3 ml IPA. Following this, 0.10156 g N-Hydroxysuccinimide (Pierce #24500) in 15 ml anhydrous IPA was prepared and 2 ml thereof was added to the threads. This reaction proceeded at 4° C. for about 48 hrs. followed by room temperature for 1 hrs., with end-over-end rotation of the vessel. The threads were then rinsed with ice-cold NaAc (10 µM, pH 5) and maintained on ice.

500 µl (1 mg) of a previously prepared avidin stock solution (in 500 µm NaHCO$_3$, pH 8.0) was added to the threads, followed by dilution with 500 µl bicarbonate buffer. This reaction proceeded for 4 hrs. at room temperature, with end-over-end rotation of the vessel, followed by maintaining the threads on ice for about 20 hrs.

Aminated polypropylene threads comprising avidin covalently attached hereto were then rinsed as follows: 2×2 ml NaHCO$_3$; 2×2 ml 0.15M NaCl; 2×2 ml HRP buffer. For convenience, these threads are referred to as "pp-avidin."

20 µl of biotinylated ILO A-206 and 20 µl trihydroxymethyl amino methane buffer (pH 7.0) were admixed with 5 mm section of pp-avidin; the reaction proceeded overnight at room temperature, followed by washing of the threads with 5×100 µl water. For convenience, these threads referred to as "pp-avidin:A-206."

5 mm section of pp-avidin:A-206 and 5 mm section of non-aminated polypropylene threads (control) were each admixed with the following: 10 µl PCR Buffer (Cetus kit); 11 µTemplate (Cetus); 69 µl water; 10 µof Master Mix (10 µl dATP, 10 µl dCTP, 10 µl dGTP, 10 µl TTP, 7.5 µl water, 2.5 µl enzyme). Enzymatic elongation of A-206 proceeded using the following cycle conditions: 35 cycles, each cycle 1 min. 55° C., 1 min. 72° C., 1 min. 94° C. Following these cycles, the threads were rinsed as follows: 3× 100 µl water; 2×100 µl Phenol/CHCl$_3$; 3×100 µl CHCl$_3$.

The phrase "enzymatic elongation" is utilized in that "amplification," as defined, is not intended per se. Rather, elongation of the immobilized ILO from the two 3' termini is expected. If this elongation occurs, then complementary sections of the template hybridizing to the ILO will be generated such that probing with allele specific oligonucleotides ("ASO") would be possible.

We selected two ASOs sequences, one complementary to nucleotides 7161–7170 of the Cetus template and the other complementary to nucleotides 7372–7381 of the template. Each ASO was labelled with adenosine 5'-[γ-$^{32}$P] triphosphate (Amersham, Cat. No. AC9303) using T$_4$ polynucleotide kinase (USB, Cat. No. 70031). Sequences were as follows:

| A-235 (nucleotides 7161–7170) (SEQ ID NO 12): |
|---|
| 5" ATG TCC GGT CAG CAC ATT TT 3" |
| A-236 (nucleotides 7372–7381) (SEQ ID NO 13): |
| 5" A CTG GCG TAA TCA TGG CCC T 3" |

Hybridization conditions with the ASOs were as follows: both the control threads and pp-avidin:A-206 (putative enzymaticly elongated) were each heated in 200 µl water at 95° C. for 20 min.; thereafter the water was removed and the threads were each placed in 20 µl of 6×SSPE buffer. Thereafter, 5 µl of labeled A-235 was added to the control threads and 5 µl of A-235 was added to pp-avidin:A-206; the reaction continued for 4 hrs. at room temperature. Thereafter, the threads were each washed with 6×100 µl of 2×SSPF buffer, followed by coonting CPMs. Counts for pp-avidin:A-206 probed with A-235 was 285. Thereafter, these ASO-bound threads were each heated in 200 µl water at 95° C. for 20 min. to remove substantially all of the bound ASOs. These threads were then probed with labeled A-236 under the conditions set forth for labeled A-235, rinsed as described, followed by obtaining CPMs. For pp-avidin:A-206 probed with labeled A-236, counts were 1,015; for control threads probed with A-236, counts were 197. This is a ratio of approximately 5:1.

Probing with the A-235 ASO was also conducted with streptavidin coated magnetic beads (Dynabeads®M-280, Prod. No. 112.05). Manufacturer instructions were followed for preparation of the support material. Attachment of biotinylated ILO (A-206) to the magnetic beads was accomplished as described above (these are referred to as "mag.-A-206"; control beads are referred to as "mag."). Approximately equivalent amounts of mag.-A-206 and mag. were utilized.

To both mag.-A-206 and mag., the following was added: PCR Buffer (Cetus kit), 10 µl ; Template, 1 µl ; Amplicon Template, 5 µl ; water, 74 µl ; 10 µl of Master Mix (8 µl dATP, 8 µl dCTP, 8 µl DGTP, 8 µl TTP, 38 µl water, 2 µl Taq enzyme). Thermocycling was as described above, followed by the same washing and hybridization conditions as described above, using the $^{32}$P-labelled ASO designated A-235.

CPM counts were as follows: mag.-A-206, 1,460; mag., 342. This evidenced a ratio of 4:1.

These results indicate that solid-phase elongation of ILO using a target sequence is viable; in essence, the target is "amplified" and the presence thereof in, e.g., a clinical sample, can be determined by probing with ASOs as disclosed.

While the foregoing has been set forth in detail, the Examples are presented for elucidation, and not limitation. Modifications and improvements on the technology disclosed above which are within the purview and abilities of those in the art are included within the scope of the following claims.

What is claimed:

1. A process for the amplification of a double-stranded nucleic acid molecule, said molecule comprising a strand and a complementary strand, comprising the steps of:

(a) separating the strand from the complementary strand;

(b) treating the strand and the complementary strand to at least one 3'-Inverse Linkage Oligonucleotide, where each 3'-Inverse Linkage Oligonucleotide comprises a first sequence portion complementary to a region on said strand and a second sequence portion complementary to a region on said complementary strand, where said regions are not complementary with each other, under conditions sufficient to permit the first sequence portion of said 3'-Inverse Linkage Oligonucleotide to hybridize to said region on said strand or the second sequence portion of said 3'-Inverse Linkage Oligonucleotide to hybridize to said region on said complementary strand;

(c) extending said hybridized 3'-Inverse Linkage Oligonucleotide with a polymerase along said strand or said complementary strand, respectively, to form 3'-Inverse Linkage Oligonucleotide products, wherein each of said products includes a segment capable of hybridizing to the portion of the 3'-Inverse Linkage Oligonucleotide not hybridized in step (b);

(d) separating 3'-Inverse Linkage Oligonucleotide products from the strand and the complementary strands to form single-stranded products, wherein at least one 3'-Inverse Linkage Oligonucleotide product has a first 3'-termini complementary to a second 3'-termini, said first 3'-termini capable of hybridizing to said second 3'-termini to form a partially double-stranded circle;

(e) treating the single-stranded products of step (d) with the 3'-Inverse Linkage Oligonucleotide of step (b) and allowing said first and second 3'-termini to hybridize to form said partially double-stranded circle; and (f) extending the 3'-Inverse Linkage Oligonucleotide and the appropriate 3'-termini of said circle with a polymerase.

2. The process of claim 1 wherein said 3'-Inverse Linkage Oligonucleotide comprises a label.

3. The process of claim 2 wherein said label is located at an inverse linkage of said 3+-Inverse Linkage Oligonucleotide.

4. The process of claim 1 wherein the length of said 3'-Inverse Linkage Oligonucleotide is between about 8 and about 100 nucleotides.

5. The process of claim 1 wherein said macromolecule is human genomic DNA.

6. The process of claim 1 wherein said 3'-Inverse Linkage Oligonucleotide products are selected from the group consisting of 3'-Inverse Linkage Oligonucleotide Amplicons, Multimeric 3'-Inverse Linkage Oligonucleotide Amplicons, and Circular Double-Stranded 3'-Inverse Linkage Oligonucleotide Amplicons.

7. The process of claim 6 wherein said 3'-Inverse Linkage Oligonucleotide Amplicons are selected from the group consisting of Partially Extended 3'-Inverse Linkage Oligonucleotide Amplicons and Fully Extended 3'-Inverse Linkage Oligonucleotides Amplicons.

8. An ILO amplification product obtained by the process of claim 1, said product comprising circular double stranded ILO amplicons.

9. A process for detecting the presence of a double-stranded nucleic acid molecule, said molecule comprising a strand and a complementary strand, comprising the steps of:

(a) separating the strand from the complementary strand;

(b) treating the strand and the complementary strand to at least one immobilized 3'-Inverse Linkage Oligonucleotide, wherein said 3'-Inverse Linkage Oligonucleotide comprises at least one inverse linkage, said 3'-Inverse Linkage Oligonucleotide being immobilized to a solid support, where each 3'-Inverse Linkage Oligonucleotide comprises a first sequence portion complementary to a region on said strand and a second sequence portion complementary to a region on said complementary strand, where said regions are not complementary to each other, under conditions sufficient to permit said 3'-Inverse Linkage Oligonucleotide to hybridize to hybridization member selected from the group consisting of:
  (i) said strand,
  (ii) said complementary strand, and
  (iii) said strand and said complementary strand;

(c) extending said 3'-Inverse Linkage Oligonucleotide with a polymerase along the region of hybridization to form extended immobilized 3'-Inverse Linkage Oligonucleotides, each of which includes a segment capable of hybridizing to the portion of the 3'-Inverse Linkage Oligonucleotide not hybridized in step (b);

(d) separating said hybridization member from said extended immobilized 3'-Inverse Linkage Oligonucleotide;

(e) detecting said extended immobilized 3'-Inverse Linkage Oligonucleotide as an indication of the presence of said molecule.

10. The process of claim 9 wherein the presence of a specific sequence is detected on said extended, immobilized 3'-Inverse Linkage Oligonucleotide said specific sequence being different than said first sequence portion complementary to a region on said strand and a second sequence portion complementary to a region on said complementary strand of said 3'-Inverse Linkage Oligonucleotide.

11. The process of claim 9 wherein said detection is by means of an allele specific oligonucleotide (ASO).

12. The process of claim 11 wherein said ASO is labelled.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:1:

GAT GAG TTC GTG TCC GTA CAA CTG G    25

( 2 ) INFORMATION FOR SEQ ID NO:2:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: yes ( x i ) SEQUENCE DESCRIPTION: SEQ ID NO:2:

GGT TAT CGA AAT CAG CGA CAG CGC C    25

( 2 ) INFORMATION FOR SEQ ID NO: 3:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: no (i v) ANTI-SENSE: partial (x i) SEQUENCE DESCRIPTION: SEQ ID NO:3:

GGT CAA CAT GCC TGT GCT TGA GTA G 25

GGT TAT CGA AAT CAG CCA CAG CGC C 25

(2) INFORMATION FOR SEQ ID NO:4:

(i) SEQUENCE CHARACTERISTICS:
        (A) LENGTH: 50 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: no (i v) ANTI-SENSE: partial (x i) SEQUENCE DESCRIPTION: SEQ ID NO:4:

C CGC GAC ACC GAC TAA AGC TAT TGG G 26

ATG AGT TCG TGT CCG TAC AAC TGG 50

(2) INFORMATION FOR SEQ ID NO:5:

(i) SEQUENCE CHARACTERISTICS:
        (A) LENGTH: 48 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: no (i v) ANTI-SENSE: partial (x i) SEQUENCE DESCRIPTION: SEQ ID NO:5:

CA CGG TCC GTA TTA GGT CCT TTT G 24

G TTG GCA TGC TTT GAT GAC GCT TC 48

(2) INFORMATION FOR SEQ ID NO:6:

(i) SEQUENCE CHARACTERISTICS:
        (A) LENGTH: 24 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: no (i v) ANTI-SENSE: no (x i) SEQUENCE DESCRIPTION: SEQ ID NO:6:

GTT TTC CTG GAT TAT GCC TGG CAC 24

(2) INFORMATION FOR SEQ ID NO:7:

(i) SEQUENCE CHARACTERISTICS:
        (A) LENGTH: 24 bases

-continued ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:7:

GTT GGC ATG CTT TGA TGA CGC TTC                   24

( 2 ) INFORMATION FOR SEQ ID NO:8:

( i ) SEQUENCE CHARACTERISTICS:
      ( A ) LENGTH: 36 bases
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: no ( i v ) ANTI-SENSE: partial ( x i ) SEQUENCE DESCRIPTION: SEQ ID NO:8:

GAT ATC ACT CAG CAT AAA TT AAC                    23
CCT CTC ACT AAA G                                 36

( 2 ) INFORMATION FOR SEQ ID NO:9:

( i ) SEQUENCE CHARACTERISTICS:
      ( A ) LENGTH: 19 bases
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:9:

ATT AAC CCT CTC ACT AAA G                         19

( 2 ) INFORMATION FOR SEQ ID NO:10:

( i ) SEQUENCE CHARACTERISTICS:
      ( A ) LENGTH: 17 bases
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: no ( i v ) ANTI-SENSE: yes ( x i ) SEQUENCE DESCRIPTION: SEQ ID NO:10:

AAT ACG ACT CAC TAT AG                            17

( 2 ) INFORMATION FOR SEQ ID NO:11:

( i ) SEQUENCE CHARACTERISTICS:
      ( A ) LENGTH: 49 bases
      ( B ) TYPE: nucleic acid

```
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: partial, biotinylated ( x i ) SEQUENCE DESCRIPTION: SEQ ID NO:11:

GGT CAA CAT GCC TGT GCT TGA GTA GGT                                27

TAT CGA AAT GAG CCA CAG CGC C                                      49

( 2 ) INFORMATION FOR SEQ ID NO:12:

( i ) SEQUENCE CHARACTERISTICS:
                ( A ) LENGTH: 20 bases
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:12:

ATG TCC GGT CAG CAC ATT TT                                         20

( 2 ) INFORMATION FOR SEQ ID NO:13:

( i ) SEQUENCE CHARACTERISTICS:
                ( A ) LENGTH: 20 bases
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:13:

A CTG GCG TAA TCA TGG CCC T                                        20
```